(12) United States Patent
Nocek

(10) Patent No.: US 11,510,956 B2
(45) Date of Patent: Nov. 29, 2022

(54) ANTIMICROBIAL PREPARATION FROM FERMENTATION YEAST PRECIPITATE

(71) Applicant: James Nocek, Skaneateles, NY (US)

(72) Inventor: James Nocek, Skaneateles, NY (US)

(*) Notice: Subject to any disclaimer, the term of this patent is extended or adjusted under 35 U.S.C. 154(b) by 0 days.

(21) Appl. No.: 17/038,582

(22) Filed: Sep. 30, 2020

(65) Prior Publication Data

US 2021/0008144 A1  Jan. 14, 2021

Related U.S. Application Data

(62) Division of application No. 16/469,684, filed as application No. PCT/US2017/066704 on Dec. 15, 2017, now Pat. No. 10,828,344.

(60) Provisional application No. 62/434,767, filed on Dec. 15, 2016.

(51) Int. Cl.
| | | |
|---|---|---|
| A61K 36/87 | (2006.01) | |
| A23K 40/10 | (2016.01) | |
| A23K 50/42 | (2016.01) | |
| A23K 50/75 | (2016.01) | |
| A23K 10/12 | (2016.01) | |
| A23K 10/14 | (2016.01) | |
| A23L 33/14 | (2016.01) | |
| C12C 11/00 | (2006.01) | |
| C12G 1/08 | (2006.01) | |

(52) U.S. Cl.
CPC .............. *A61K 36/87* (2013.01); *A23K 10/12* (2016.05); *A23K 10/14* (2016.05); *A23K 40/10* (2016.05); *A23K 50/42* (2016.05); *A23K 50/75* (2016.05); *A23L 33/14* (2016.08); *C12C 11/00* (2013.01); *C12G 1/08* (2013.01); *A23V 2002/00* (2013.01)

(58) Field of Classification Search
None
See application file for complete search history.

(56) References Cited

U.S. PATENT DOCUMENTS

| | | | |
|---|---|---|---|
| 6,387,417 B1 | 5/2002 | Iwai | |
| 6,548,076 B2 | 4/2003 | Shanbrom | |
| 8,236,303 B2 | 8/2012 | Forsberg et al. | |
| 10,828,344 B2 * | 11/2020 | Nocek | A23K 40/10 |
| 2003/0108493 A1 | 6/2003 | Henry et al. | |
| 2003/0198699 A1 | 10/2003 | Shanbrom | |
| 2006/0078568 A1 | 4/2006 | Pauly et al. | |
| 2011/0256232 A1 | 10/2011 | Nygaard et al. | |
| 2012/0009280 A1 | 1/2012 | Houseman et al. | |
| 2015/0328274 A1 | 11/2015 | Kappagoda et al. | |
| 2015/0366238 A1 | 12/2015 | Elend | |
| 2020/0222489 A1 | 7/2020 | Nocek | |

FOREIGN PATENT DOCUMENTS

| | | | |
|---|---|---|---|
| CN | 102871092 | * | 1/2013 |
| CN | 104435062 A | | 3/2015 |
| JP | 2007099718 A | | 4/2007 |
| KR | 888492 | * | 3/2009 |

OTHER PUBLICATIONS

International Search Report and Written Opinion of the International Searching Authority for PCT/US2017/066704 dated Mar. 26, 2018.
Integral A+ Products, Hubbard Feeds Inc., OptiCare, Optimum Health and Performance http://www.hubbardfeeds.com.
Nocek, J.E., et al., "Effects of supplementation with yeast culture and enzymatically hydrolyzed yeast on performance of early lactation dairy cattle", J. Dairy. Sci., No. 94, pp. 4046-4056 (2011).
Smit, A.Y., et al., "Biogenic Amines in Wine: Understanding the Headache", S. Afr. J. Enol. Vitic., vol. 29, No. 2, pp. 109-127 (2008).
International Preliminary Report on Patentability for PCT/US2017/066704 dated Jan. 17, 2019.
Perez-Bibbins, B. et al. Potential of Lees from Wine, Beer and Cider Manufacturing as a source of Economic Nutrients: An Overview. Waste Management 40:72-81, Jun. 2015.

* cited by examiner

*Primary Examiner* — Ralph J Gitomer
(74) *Attorney, Agent, or Firm* — Heslin Rothenberg Farley & Mesiti P.C.

(57) ABSTRACT

Provided are methods of making and using an antimicrobial composition, optionally including adding one or more enzymes to a suspension of lees, wherein the lees was formed by fermenting fruit with yeast and the one or more optional enzymes comprise a protease, a carbohydrase, or a combination of a protease and a carbohydrase; and forming a dried lees by drying the lees. In some examples the fruit includes chardonnay grapes, pinot noir grapes, cabernet franc grapes, or a combination of any two or more of chardonnay grapes, pinot noir grapes, and cabernet franc grapes; the yeast includes one or more *Saccharomyces cerevisiae* strains of yeast; and drying the lees by heating it. In some examples, trub made from fermenting a grain such as barley is used instead of lees. An antimicrobial composition made as provided may be administered to an animal to inhibit bacterial growth.

23 Claims, 4 Drawing Sheets

ANTIMICROBIAL PREPARATION FROM FERMENTATION YEAST PRECIPITATE

CROSS-REFERENCE TO RELATED APPLICATIONS

This application is a divisional of non-provisional U.S. patent application Ser. No. 16/469,684, which was filed on Jun. 14, 2019, as a National Stage Entry under 35 U.S.C. § 371 from Application No. PCT/US2017/066704, which was filed on Dec. 15, 2017, which claims priority under 35 U.S.C. § 119 to U.S. Provisional Application No. 62/434,767, filed Dec. 15, 2016, which applications are herein incorporated by reference in their entireties.

FIELD OF THE INVENTION

The present invention relates to, inter alia, prebiotic compositions made from fermentation by-products possessing antimicrobial qualities and methods for the manufacture and use thereof.

BACKGROUND OF THE INVENTION

Prebiotics, in particular yeast derivatives including yeast cell wall components are promising supplements for improved health and alternatives to antibiotics with respect to the promotion of health and performance in vertebrates, including humans and livestock, based on their capacity to bind enteropathogenic bacteria and to beneficially modulate the immune system. An important initial event in bacterial pathogenesis is the adherence of bacteria via their surface lectins to host intestinal cells: infections are initiated only after the microorganism has first adhered to the host cell surface. If this initial adherence can be inhibited, so can the subsequent infection. Inhibiting such processes is animals such as cattle, swine, fowl, or other mammals or birds improves their health, which in turn improves their utility as sources of food, and also improves human health by preventing transmission of a bacterial infection from an animal which has contracted it to a human, such as through consumption of meat from animals which have contracted bacterial infection. Inhibiting such processes in humans also may promote human health by preventing infection.

An initial event in bacterial pathogenesis may be the adherence of bacteria via their surface lectins to host intestinal cells: infections are initiated only after the microorganism has first adhered to the host cell surface. If this initial adherence can be inhibited, so can the subsequent infection. This approach forms the basis of anti-adherence strategies with the most studied being receptor-analogs, which include oligosaccharides to which enterobacterial cells bind. Such binding may prevent binding to intestinal cells and, thus, infection. Furthermore, the pathogenic enterobacteria so bound to a ligand such as an oligosaccharide may act as an antigen. The sequestered antigen is detected by the immune system and an "alert" is triggered by the innate immune system at lower levels of challenge. The system is "alarmed" at higher levels of challenge system can "mount" an immune response, whereby it enters and "attack/defend" mode. Finally the "adaptive" system can initiate a "surveillance" to continue to mount a response to subsequent challenges.

Yeast cell wall (YCW) products are suggested as anti-adhesive agents and are thus proposed to prevent attachment of certain intestinal bacteria. The YCW provides alternative adhesion sites to enterobacteria, which contain mannose-specific type I fimbriae such as *Escherichia coli* or *Salmonella* spp. and which is well documented. In order for the pathogen to adhere to the mannose (or a YCW ligand), such ligand must be physically exposed and accessible to the organism. Therefore, processing YCW to expose the ligand may provide a qualitative enhancement to YCW's effectiveness as a prebiotic.

In the process of vinification, yeast is added to components of fruit, such as grapes for alcoholic fermentation. Different yeast strains are used for different grape and wine varietal types. When the initial fermentation is complete, the fermented juice is racked off a precipitate referred to as lees, which contains residual yeast components. A similar process is used in brewing beer, with the residual yeast precipitate formed during brewing referred to as lees or trub. Lees and trub contain some fruit sugar residues, various carbohydrate substrates, end products of fermentation, acids and spent yeast cells. They are typically considered a waste product of the winemaking and brewing processes and conventionally are discarded. Lees may therefore provide a usable source of previously untapped YCW, such as for use as antimicrobial preparations. A method is therefore needed for preparing antimicrobial agents from lees.

In the wine making process, the typical yeast addition for alcoholic fermentation is 1 g/gallon of juice. Different yeast strains are used for different grape and wine varietal types. When the initial fermentation is complete, the fermented juice (wine) is racked off the lees. The lees contains some grape sugar residues, various carbohydrate substrates, end products of fermentation, acids and spent yeast cells. In addition, lees from certain grape varieties (reds in particular) have shown to be rich in various phenolic compounds that provide antioxidant properties. Lees are typically considered a waste product of the industry and are discarded. The craft and commercial wine industry has exploded in the past 20 years, thus producing a considerable waste stream in the form of lees. The advantage of YCW from alcoholic fermentation: more and different chemical moieties that are highly biologically active as anti-adhesive agents because of their potential physical exposure to pathogenic type 1 fimbriae.

SUMMARY OF THE INVENTION

The present disclosure relates to, inter alia, a method of making an antimicrobial composition including adding one or more enzymes to a suspension of lees, wherein the lees was formed by fermenting fruit with yeast and the one or more enzymes comprise a protease, a carbohydrase, or a combination of a protease and a carbohydrase; and forming a dried lees by drying the lees.

Also provided is a method of making an antimicrobial composition including adding one or more enzymes to a suspension of lees, wherein the lees was formed by fermenting fruit with yeast; the one or more enzymes include a protease, a carbohydrase, or a combination of a protease and a carbohydrase; the fruit includes chardonnay grapes, pinot noir grapes, cabernet franc grapes, or a combination of chardonnay grapes, pinot noir grapes, and cabernet franc grapes; the yeast includes one or more *Saccharomyces cerevisiae* strains of yeast; and drying the lees by heating it.

In some examples, no enzymes are added. In other examples, trub, made from fermenting a grain such as barley, is used in place of lees.

In other aspects, an antimicrobial composition made according to methods disclosed herein is administered to an animal to inhibit bacterial growth in said animal. The animal may be a mammal, such as a cow, ox, horse, goat, pig, sheep, horse, mule, donkey, deer, llama, cat, or dog, or other mammal. The animal may be a primate, such as a human. The animal may be a bird, such as a chicken, turkey, pheasant, goose, duck, quail, or other poultry.

BRIEF DESCRIPTION OF THE DRAWINGS

For the purpose of illustrating aspects of the present invention, there are depicted in the drawings certain embodiments of the invention. However, the invention is not limited to the precise arrangements and instrumentalities of the embodiments depicted in the drawings. Further, as provided, like reference numerals contained in the drawings are meant to identify similar or identical elements. The foregoing and other objects, features, and advantages of the invention are apparent from the following detailed description taken in conjunction with the accompanying drawings in which.

DETAILED DESCRIPTION OF THE INVENTION

Figure 1:
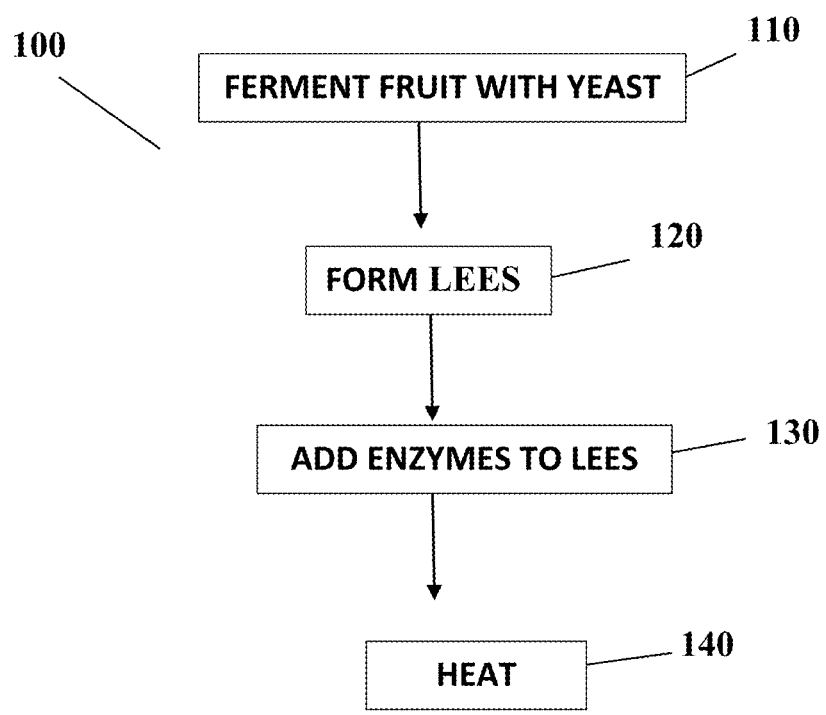
FIG. 1 is a block diagram depicting a method for manufacturing a composition made from lees possessing antimicrobial qualities in accordance with the present disclosure.

Aspects of an invention disclosed herein and certain features, advantages, and details thereof, are explained more fully below with reference to the non-limiting embodiments illustrated in the accompanying drawings. Descriptions of well-known materials, fabrication tools, processing techniques, etc., are omitted so as to not unnecessarily obscure the invention in detail. It should be understood, however, that the detailed description and the specific examples, while indicating some embodiments, are given by way of illustration only, and are not by way of limitation. Various substitutions, modifications, additions and/or arrangements within the spirit and/or scope of the underlying inventive concepts will be apparent to those skilled in the art from this disclosure.

The present disclosure relates to, inter alia, an antimicrobial preparations made from lees (or other YCW-containing fermentation by-product) and a method for the manufacture thereof. In an embodiment, lees is produced by fermenting fruit juice by the addition of yeast. Lees, containing yeast components, including YCW (or comparable YCW-containing by-product from fermentation performed for reasons other than vinification), is then harvested and, optionally, treated with enzymes to expose mannose and other residues present in the YCW. Lees is then dried, forming a dried lees composition. The dried lees composition is an antimicrobial composition, showing potent antimicrobial properties including an ability to agglutinate enteropathogenic bacteria, bactericidal properties, and bacteriostatic properties. As skilled artisans would appreciate, yeast residue may also be obtained following fermentation of other materials, including, as non-limiting examples, malt (such as, but not limited to, in the production of beer or whiskey), molasses (such as, but not limited to, in the production of rum), honey (such as, but not limited to, in the production of mead), meal (such as, but not limited to, in the production of ethanol from fermentation of corn), cellulose fiber (such as, but not limited to, in the production of cellulosic ethanol), grains (such as wheat, rye, barley, rice, oat, etc.), or other sugar-containing materials or sugar-based substrate. Preparation and use of YCW from yeast residue from lees, trub, or other examples from among the foregoing non-exhaustive list are explicitly included as part of the presently disclosed invention, said compositions possessing antimicrobial properties disclosed herein.

In some aspects, lees may be produced by fermentation of grape juice. Many different varietals of grapes may be used, including as non-limiting examples chardonnay, pinot noir, cabernet sauvignon, cabernet franc, grenache, malbec, merlot, riesling, sauvignon blanc, semillon, syrah, tempranillo, viognier, and any combination of any two or more thereof. In one example, chardonnay grapes are used. In another example, pinot noir grapes are used. In yet another example, cabernet franc grapes are used. It will be understood, however, that other grape varietals, or other fruits, could be used in accordance with a method disclosed herein, as could combinations thereof.

In other aspects, yeast used in fermentation may include as non-limiting examples a *Saccharomyces* yeast strain, a *Brettanomyces* yeast strain, a *Candida* yeast strain, a *Kloeckera* yeast strain, a *Saccharomyces* yeast strain, a *Schizosaccharomyces* yeast strain, an *Aureobasidium* yeast strain, and any combination of two or more thereof. In some examples, a *Saccharomyces* strain of yeast may be used, including as non-limiting examples a strain of *Saccharomyces cerevisiae* yeast, a strain of *Saccharomyces bayanus* yeast, a strain of *Saccharomyces beticus* yeast, a strain of *Saccharomyces fermentati* yeast, a strain of *Saccharomyces paradoxus* yeast, a strain of *Saccharomyces pastorianus* yeast, a strain of *Saccharomyces uvarum* yeast, or any combination of two or more thereof may be used. In a non-limiting example, a strain or strains of *Saccharomyces cerevisiae* yeast may be used. Skilled artisans would appreciate that other types or strains of yeast could likewise be used in accordance with the method disclosed herein.

In another aspect, lees may be, optionally, treated with an enzyme or enzymes. For example, lees may be treated with a peptidase or peptidases (such as an acid peptidase and/or other peptidase(s)), a carbohydrase (such as a pectinase and/or other carbohydrase(s)), or a combination of peptidase(s) and carbohydrase(s), simultaneously or in succession. Such enzymatic processing exposes inner cell wall carbohydrates of YCW, such as mannan oligosaccharides, to present ligand binding sites for microbes. Examples of enzymes suitable for such processing include, as non-limiting examples, acid proteases, fungal proteases such as HUT and AV, alone or in combination, as non-limiting examples, cellulases, xylanases, and hemicellulases, as non-limiting examples. For example, lees harvested following vinification or trub harvested following brewing (or other YCW-containing by-product of other fermentation performed for reasons other than brewing beer or vinification) may be suspended in aqueous or other solution and combined with an enzyme or enzymes to promote break-up of YCW and exposure of moieties, including mannan oligosaccharides, to permit binding or attachment to microbes, including enterobacteria. In other examples, lees is prepared and dried without enzyme treatment.

In other examples, lees may be heated (without drying) or dried (without heating), or dried by application of heat. Heating or drying, or both (such as drying by applying heat), of antimicrobial agents may confer advantageous qualities. If an antimicrobial agent retains its antimicrobial properties upon loss of water or other moisture, the reduction in volume resulting from drying facilitates storage. It may also render the composition more stable, permitting more prolonged storage and greater ease of distribution and at lower cost. A dried composition may also be ground into a granular or powdered form, facilitating addition thereof to animal feed at easily quantifiable doses, a beneficial quality particularly for industrial-scale husbandry where ease, reliability, and predictable costs can promote successful business practices. However, when lees is heated or dried, or dried by application of heat, and tested for its use as a prebiotic, it has shown poor antimicrobial properties. And for prebiotics in general, exposure to certain temperature ranges during processes such as drying is known to inhibit antimicrobial activity. Application of heat may confer certain advantages, such as in exposing YCW components that confer antimicrobial properties, and inhibiting or preventing the growth of unwanted contaminants such as mold, fungus, or other organisms in lees or other prebiotic preparation from a fermentation by-product. Thus, whereas heating or drying a lees or other prebiotic preparation, or both, in accordance with the present disclosure may confer advantages in preparation of a prebiotic composition, conventionally it also risks compromising antimicrobial properties of a resulting prebiotic, potentially offsetting any benefits.

Surprisingly, however, disclosed herein is a method including heating lees (or other fermentation by-product containing YCW)) to produce a prebiotic composition with potent antimicrobial activity. In accordance with the processing steps disclosed herein, and contrary to conventional expectation, heating may be performed by any method suitable for lees (or other fermentation by-product containing YCW) to an elevated temperature and result in formation of a robustly antimicrobial product. For example, lees or similar preparations may be exposed to temperatures between 90° F. and 200° F. while preserving biological activity against a substantial variety of antimicrobial agents, such as disclosed herein. In some embodiments, lees or similar preparations may be exposed to temperatures between 100° F. and 190° F., or temperatures between 110° F. and 180° F. In other embodiments, lees or similar preparations may be exposed to a temperature of 95° F., 100° F., 105° F., 110° F., 115° F., 120° F., 125° F., 130° F., 135° F., 140° F., 145° F., 150° F., 155° F., 160° F., 165° F., 170° F., 175° F., 180° F., 185° F., 190° F., 195° F., or 200° F., or a temperature or temperatures within a range or ranges that is or are between any two of any of the foregoing temperatures. For example, lees or similar preparations may be exposed to a temperature or temperatures within a range of 90° F. to 200° F., or of 100° F. to 190° F., or of 110° F. to 180° F., or of 120° F. to 170° F., or of 130° F. to 160° F., or of 140° F. to 150° F., or of 100° F. to 150° F., or of 150° F. to 200° F., or of 110° F. to 130° F., or of 120° F. to 140° F., or of 130° F. to 150° F., or of 140° F. to 160° F., or of 150° F. to 170° F., or of 160° F. to 180° F., or of 170° F. to 190° F., or of 180° F. to 200° F., or other temperature ranges derivable from these examples.

In some examples, lees or other preparations may be dried by removing fluid or liquid, such as exposure to air for passive evaporation, exposure to heating elements such as an oven or heating lamp, or exposure to low vacuum pressure, spray drying, drum drying, extrusion drying, or any combination of the foregoing. In some examples, dried lees may be ground or otherwise processed into a granular or powder form. Drying lees or other YCW-containing fermentation by-product may permit easier storage and allows expanded usage at lower concentrations than otherwise possible, enabling advantageously improved utility. In some examples, drying may include exposure to heat. In such examples, a drying temperature may be employed in drying lees as disclosed herein without sacrifice of potent antimicrobial activity, resulting in a prebiotic compound that is highly effective at low doses or concentrations relative to other prebiotics.

A preparation may be dried by removal of water or moisture, which may facilitate storage, use, transport, and/or administration of a prebiotic preparation. It may enable formation of a powder or granulated form, or storage in capsules such as for oral consumption, or easier measurement such as for determining consistent amounts for ingestion (as non-limiting examples as a powder, encapsulated powder, or dried powder mixed with food). Drying may be measured by determining a relative amount of water or moisture that remains in a preparation after performing a drying process. For example, a preparation may be dried such that it contains less than a specified w/w percentage of water. In some examples, it may contain less than 10%, less than 5%, or less than 1% w/w water. In other examples, more water may be retained, such as if a preparation is somewhat dried to increase a relative proportion of some components at the expense of removal of some liquid but retaining some water. In some examples, a wet lees preparation may be formed, following incomplete or minimal drying, such as to form a concentrated, wet preparation. In still other examples, a preparation may be dried then rehydrated by the re-addition of water.

As would be appreciated by skilled artisans, various methods for assessing antimicrobial activity of a prebiotic may be used, including in vitro evaluations which may provide predictions of in vivo activity and utility as an antimicrobial agent, food additive, supplement, or alternative to antibiotic treatment (e.g., as a feed additive as an alternative to prophylactic antibiotic use in animals, and/or as supplements for humans to promote improved gastrointestinal or health and/or immune function). For example, in vitro tests of a putative prebiotic's ability to agglutinate enterobacteria can indicate whether such composition would be effective in sequestering enterobacteria in the gastrointestinal tract and diminish the binding of microbes to the cell walls of a host animal and thereby prevent infection. Tests of compositions ability to inhibit growth of microbes such as enterobacteria may further indicate bacteriostatic effects (i.e., an ability to prevent growth of bacteria) and/or bactericidal effects (i.e., an ability to kill bacteria). By determining a minimum inhibitory concentration of a prebiotic necessary to have a given effect, and comparing the minimum effective concentrations of different potential prebiotics to each other, relative potencies for in vive effectiveness for the prevention of infection may be determined. As is known to skilled artisans, effectiveness of prebiotics, such as YCW preparations or compositions including YCW as a constituent, may be compared to the effectiveness of antibiotics in similar manner. Comparison of in vitro testing between different preparations can provide a high degree of confidence of the effectiveness, and relative effectiveness, of such preparations on preventing infection or otherwise promoting health in vivo.

In FIG. 1, shown is an example of a method for producing a prebiotic yeast preparation from a fermentation product 100. A fermentation process 110 is performed by fermenting fruit with yeast. In some examples, the fruit may be a grape varietal and the yeast may be a strain of *S. cerevisiae*. In some examples, rather than a fermentation process being performed as part of a method as disclosed herein, by-products of such a process are simply obtained. Lees 120, or other YCW-containing by-product of a fermentation process, is formed by a fermentation process or obtained after the performance of such a process. In this example, enzymes, such as peptidases and/or carbohydrases are added to the lees 130. In other examples, enzymes are not added. The lees is then heated, at a temperature or temperature or temperature range between 90° F. and 200° F. 140. In some examples, the heated lees may be dried by removal of water, such that the preparation contains less than 95% w/w water.

A method of inhibiting bacterial growth in an animal is also provided. An antimicrobial composition synthesized as disclosed herein (e.g., made from lees or trub according to any of the various examples disclosed herein) may be administered to an animal and thereby inhibit bacterial growth in the animal. For example, the preparation may be fed to the animal. The animal may be a mammal, such as a cow, ox, horse, goat, pig, sheep, horse, mule, donkey, deer, llama, dog, or cat, or other mammal. The animal may be a primate, including a human. The animal may be a bird, such as a chicken, turkey, pheasant, goose, duck, quail, or other poultry. As skilled artisans would appreciate from the antimicrobial properties of preparation made by methods herein disclosed, administration of such compositions would be understood to inhibit bacterial growth when brought into contact with susceptible microbes, including within the digestive tracts of animals, including without limitation the foregoing identified animals.

EXAMPLES

The following examples are intended to illustrate particular embodiments of the invention disclosed herein, but are by no means intended to limit the scope of the present invention.

Although preferred embodiments have been depicted and described in detail herein, it will be apparent to those skilled in the relevant art that various modifications, additions, substitutions, and the like can be made without departing from the spirit of the invention disclosed herein and these are therefore considered to be within the scope of said invention as defined in the claims that follow.

Test Article Preparation

Lees was prepared as follows. Chardonnay grapes (CH) were inspected and received 40 ppm SO2, whole cluster pressed, cold settled in stainless steel (1000 gallon) tanks, racked, and warmed to 650 F. Juice was inoculated with a cultured yeast at approximately 1 gm/gallon of juice. The alcoholic fermentation lasted approximately 14 days, at which time the fermentation was killed by dropping the temperature to 320 F. Wine was racked and the remaining solids was classified as lees. In addition, Pinot Noir grapes (PN) were inspected and 30 ppm of SO2 was added. Grapes were then macerated and destemmed. Macerated grapes were placed in 4'×4'×4' plastic bins. They were inoculated with a cultured yeast strain and fermented to dryness. The contents were loaded into a diaphragm press, pressed, and the fermented juice was transported to stainless steel tanks where the temperature was dropped to 320 F. Wine was racked and the remaining solids was classified as lees.

Lees were rinsed with water from the tank with approximately 3 times their volume. The slurry was allowed to settle, water was decanted, and a second rinse process was imposed. Lees were sampled for pH and dry matter determination. Dry matter was determined in a forced are oven at 120° F., pH was determined by a pH meter.

Enzymes cocktails were selected to digest protein cross-links within the YCW of the lees, allowing greater exposure of the inner cell wall carbohydrate moieties. The following enzymes were obtained from BIO-CAT, Troy, Va.: Acid Protease 4,000 SAP/g, Fungal Protease HUT and AV Blend (Cellulase 100,000 CU, Xylanase 50,000 XU and Hemicellulase 150,000 HCU. Lees were diluted with about 3 times volume with water to create a slurry. This was done to accommodate enzyme exposure to yeast cell wall (YCW) substrate. In some examples, optimal pH of the proteases were 3.0. Slurries were acidified with citric acid (2 g citric acid/50 g lees) to accommodate optimal pH where applicable. The outer layer of the YCW is composed of a mano-protein complex which can act as a barrier to YCW carbohydrate moiety exposure. Therefore, 2 enzyme application approaches were evaluated in a preliminary evaluation:

Application 1: application of an enzyme cocktail that contained both proteases and carbohydrases.

Application 2: two phase process whereby the proteases (75% Fungal protease:25% acid protease, w/w) were exposed to the YCW initially (0.5 h), followed by exposure to the carbohydrases (0.5 g/100 g DM lees). Lees/Enzymes slurries were stirred gently post enzyme introduction. In application 1, the protease/carbohydrase cocktail was added and stirred for 1 hr. For application 2, the protease was introduced for 0.5 h, then the carbohydrase was subsequently added to the slurry and stirred for 1 h.

After enzyme application, slurries were poured onto a fluid bed and introduced into a forced air oven (120° F.) until dry. Dried slurries were then ground through a 1 mm screen Wiley mill to produce a granular preparation.

The results of a preliminary evaluation showed minimal differences in agglutination between the two application processes, therefore, application 1 (CH1 Chardonnay) and PN1 (Pinot Noir)), and no enzyme add controls (CHC (Chardonnay no enzyme add control), PNC (Pinot Noir no enzyme add control)) was used for the remaining lees products evaluations.

Comparative Commercial Products

Commercially available products were collected from feed mill outlets. All products contain YCW preparations at various levels according to tag ingredients. They were:

OMNIGEN-AF™ (OMN). Ingredient list: Silicon dioxide, calcium aluminosilicate, brewers dehydrated yeast, mineral oil, calcium carbonate, rice hulls, niacin supplement, biotin, d-calcium pantothenate, vitamin B-12, choline chloride, thiamine mononitrate, pyridoxine hydrochloride, riboflavin-5-phosphate and folic acid. Manufactured by Prince Agri Products, Quincy Ill.

INTEGRAL A+™ (INT): Hydrolyzed yeast, corn distillers dried grain with solubles, hydrated sodium calcium alumiosilicate and fat product feed grade. Manufactured by Alltech Inc., Nicholasville, Ky.

CELMANAX™ (CEL): processed grain products, hydrolyzed yeast, yeast extract, yeast culture and D&C Blue #1. Manufactured by ViCor, Mason City, Iowa.

CELMANAX™ (SCP): hydrolyzed yeast, yeast extract, yeast culture and FD&C Blue #1. Manufactured by Church and Dwight Co., Inc., Ewing, N.J.

Agglutination Procedure

Agglutination Procedure was that of Mirelmann et. al 1980. The objective of the agglutination was to determine if the test articles have agglutination activity against specific enteropathogenic organisms. The organisms were tested against each of 8 test articles at 3 different concentrations (2 mg/ml, 20 mg/ml and 40 mg/ml) along with a blank Mueller Hinton Broth (MHB), a MHB/Salmonella and a MHB/E. coli as controls.

Preparations of Inocula

The pathogens selected for the agglutination trial are well-known for posing significant threats to humans and food supply. Organisms were prepared individually from stock cultures and grown for 24 hours±2 in MHB. Once organisms were growing well they were harvested by centrifugation and the pellet resuspended in cold phosphate buffered saline (PBS). The suspension was adjusted to a standardized optical of 1.5 using the spectrophotometer at 600 nm. Bacterial suspensions were plated to Blood Agar plates to confirm the CFU/mL. Concentration results are presented in Table I below:

Preparation and Inoculation of Samples (Test Articles)

The test articles were prepared at 3 concentrations: 2, 20 and 40 mg/mL along with a blank MHB, MHB/E. coli and MHB/Salmonella as controls. The test articles were diluted to the appropriate concentrations in sterile PBS at a concentration of 40 g/L (40 mg/mL). The 20 and 2 mg/mL were made by diluting portions of this solution.

Agglutination Analysis

One drop (25 µl) of each bacterial suspension was mixed on a slide with one drop (25 µl) of each test article product. Samples were rotated for 5 minutes. Visual sample results were recorded as one of the following: negative, microscopically positive (MP). ±reaction, 1+, 2+, 3+, or 4+. The scales goes from ±(slight grainy appearance or very little agglutination) to 4 (highest agglutination-large clumps). Samples that did not show agglutination were scored as negative. Negative samples were looked at microscopically for evidence of clumping. The designations were converted to % Agglutination as follows: Neg=0, MP=17%, ±=33%, 1=50%, 2=67%, 3=83% and 4=100%.

Results

Agglutination of E. coli Strains

Agglutination effects for E. coli are presented in Table II and further summarized below:

TABLE 2

Effect of Product Concentration on E. Coli Strain Agglutination

| E. Coli Strain | Lees Products | | | | Commercial Products | | | | SEM |
|---|---|---|---|---|---|---|---|---|---|
| | CHC | PNC | CH1 | PN1 | CEL | SCP | OMN | INT | |
| E. Coli O157:H7 | | | | | | | | | |
| 40 mg | 0 c | 17 b | 33 a | 33 a | 0 c | 0 c | 0 c | 0 c | 2 |
| 20 mg | 0 b | 0 b | 25 a | 17 a | 0 b | 0 b | 0 b | 0 b | 2.8 |
| 2 mg | 0 | 0 | 0 | 0 | 0 | 0 | 0 | 0 | 0 |
| E. Coli F18 | | | | | | | | | |
| 40 mg | 75 a | 75 a | 83 a | 83 a | 0 d | 33 b | 83 a | 17 c | 4 |
| 20 mg | 67 ab | 50 b | 83 a | 67 ab | 0 c | 17 c | 67 ab | 17 c | 5.8 |
| 2 mg | 17 b | 17 b | 17 b | 42 a | 0 c | 17 b | 42 a | 17 b | 4.3 |
| E. Coli K88 | | | | | | | | | |
| 40 mg | 0 c | 42 a | 17 b | 0 c | 0 c | 17 b | 50 a | 0 c | 3 |
| 20 mg | 0 b | 17 a | 17 a | 0 b | 0 b | 17 a | 9 ab | 0 b | 3 |
| 2 mg | 0 | 17 | 9 | 0 | 0 | 9 | 25 | 0 | 11.4 |
| E. Coli K99 | | | | | | | | | |
| 40 mg | 83 ab | 83 ab | 83 ab | 83 ab | 0 c | 83 ab | 92 a | 75 b | 4.1 |
| 20 mg | 83 a | 75 a | 83 a | 83 a | 0 d | 75 a | 17 c | 50 b | 4 |
| 2 mg | 8.5 | 8.5 | 17 | 25 | 0 | 33.5 | 17 | 8.5 | 10.6 |

TABLE 1

Concentration of Bacterial Suspensions

| Sample | CFU/mL |
|---|---|
| Salmonella typhimurium (ATCC 14028) | $6.9 \times 10^8$ |
| Salmonella enterica subsp. enterica serovar Dublin (ATCC 15480) | $7.4 \times 10^7$ |
| Salmonella enterica subsp. enterica serovar Enteritidis (ATCC BAA-1045) | $7.5 \times 10^8$ |
| Salmonella enterica subsp. enterica serovar Paratyphi B (ATCC 8759) | $2.6 \times 10^8$ |
| Escherichia coli O157:H7 | $5.0 \times 10^8$ |
| Escherichia coli F18 antigen | $1.6 \times 10^9$ |
| Escherichia coli K88 antigen | $2.9 \times 10^9$ |
| Escherichia coli K99 antigen | $1.7 \times 10^9$ |

E. coli O157:H7: At the 40 mg concentration, products PN1 and CH1 showed the highest agglutination percentage at 33, significantly higher (p<0.05) than PNC (17%, Table 1). The remaining products showed 0% agglutination at 40 mg. At 20 mg, only PNC and CH1 exhibited agglutination (17 and 25%, respectively), with 0% agglutination for the remaining products. No agglutination was observed for any products at the 2 mg concentration.

E. coli F18: Highest agglutination percentage at 40 mg were between 75 and 83% for PN1, PNC, CH1, CHC and OMN: these were significantly higher (p<0.05) than SCP (33%), which was higher than INT (17%), with CEL processing 0% agglutination. Halving the concentration to 20 mg did not numerically reduce the % agglutination for CH1. PN1, PNC, and OMN were numerically (67%), but not significantly lower. PNC was significantly lower (P<05) than CH1. INT, CEL and SCP were significantly lower than others (0-17% agglutination). At 2 mg, PN1 and OMN demonstrated agglutinations of 42%, which was significantly higher (p<0.05) than the other products (17%), while CEL was 0%.

*E. coli* K 88: Agglutination at 40 mg was highest for PNC and OMN (42 and 50%), intermediate for CH1 and SCP (17%) and 0% for PN1, CHC, INT and CEL. At 20 mg, agglutination was reduced to 17% for PNC, while CH1 and SCP maintained 17%, and OMN dropped to 9%, while others yielded 0% agglutination. There were no significant differences in agglutination for this pathogen at 2 mg, numerically ranging from 0 to 17%.

*E. coli* K99: All products provided an agglutination of 75% or greater at the 40 mg concentration, except CEL, which was 0%. PN1, PNC, CH1 and CHC and SCP retained at least a 75% agglutination when the concentration was reduced to 20 mg, and were higher than INT (50%), OMN (17%), and CEL (0%). There were no significant differences in agglutination at 2 mg, numerically ranging from 0 to 33%.

Of the *E. coli* strains selected, *E. coli* 0157:H7 and F18 strains possess the most significant disease threat. *E. coli* 0157:H7 ability to induce injury in humans is a result of its ability to produce numerous virulence factors, most notably Shiga toxin (Stx), which is one of the most potent toxins known to man (Griffin and Tauxe 1991, Johannes 2010, Suh et al 1998). Shiga toxin has multiple variants (e.g., Stx1, Stx2, Stx2c), and acts like the plant toxin ricin by inhibiting protein synthesis in endothelial and other cells (Sandvig et. al 2002). Endothelial cells line the interior surface of blood vessels, and are known to be extremely sensitive to *E. coli* 0157:H7, which is cytotoxigenic to these cells (Sandvig 2002).

In addition to Shiga toxin, *E. coli* 0157:H7 produces numerous other virulence factors, including proteins which aid in the attachment and colonization of the bacteria in the intestinal wall and which can lyse red blood cells and liberate iron to help support *E. coli* metabolism (Welinder-Olsson and Kaijser 2008)

*E. coli* O157:H7 evolved from enteropathogenic *E. coli* serotype O55:H7, a cause of non-bloody diarrhea. *E. coli* O157:H7 is a relentlessly evolving organism, constantly mutating and acquiring new characteristics, including virulence factors that make the emergence of more dangerous variants a constant threat (Robins-Browne 2005, Manning et al 2008).

Although foods of bovine origin are the most common cause of both outbreaks and sporadic cases of *E. coli* O157:H7 infections, outbreaks of illnesses have been linked to a wide variety of food items. For example, Outbreaks have been linked to alfalfa, clover and radish sprouts, lettuce, and spinach (Freidman et. al 1999, Cody et al 1999). Other vehicles for outbreaks include unpasteurized juices, yogurt, dried salami, mayonnaise, raw milk, game meats, hazelnuts, and raw cookie dough (Feng 1995, Rangel et al 2005, Breuer et al. 2001)

Antibiotics do not improve the illness, and some medical researchers believe that these medications can increase the risk of developing HUS (Hemolytic Uremic Syndrome, Wong et. al. 2012). Therefore, apart from supportive care, such as close attention to hydration and nutrition, there is no specific therapy to halt *E. coli* symptoms (Tarr, 1995).

Up to 33% of the organisms subjected to PN1, PNC and CH1 did agglutinate this organism, while there was no agglutination for the existing commercial products tested. This does offer hope of attenuating the disease process through non-antibiotic means and could very well initiate the mounting for an immune response stimulating in innate and adaptive immune system. Additional dosage of these lees products may show promise in initiating a therapeutic protective response when a known challenge is anticipated. In addition, there is evidence that these types of products may be beneficial in tying up some of the shiga-toxin, once the disease process has advanced (Baines et. al. 2010).

*E. coli* F18 causes post-weaning diarrhea, also characterized by dehydration, lethargy, and wasting, often resulting in a high mortality rate. In addition, F18-positive *E coli* strains can be classified as shiga toxin-producing *E coli* (STEC) if they contain a gene that encodes for a shiga-like endotoxin (Stx2e). The Stx2e toxin is responsible for vascular damage and permeability, resulting in edema disease in pigs, characterized by generalized edema in several tissues (e.g., brain, forehead, eyelids, stomach), ataxia, lateral recumbency, dyspnea, and acute mortality (Fairbrother and Gyles 2006).

All of the lees products produced a >75% agglutination with this strain. OMN was the only commercial product that preformed in a similar fashion. Other products (SCP and INT) agglutinated <35%, and CEL exhibited 0% agglutination.

Agglutination of *Salmonella* Strains

Agglutination effects for *salmonella* are presented in Table 3 and further summarized below:

TABLE 3

Effect of Product Concentration on *Salmonella* Strain Agglutination

| *Salmonella* Strain | Lees Products | | | | Commercial Products | | | | SEM |
|---|---|---|---|---|---|---|---|---|---|
| | CHC | PNC | CH1 | PN1 | CEL | SCP | OMN | INT | |
| S. Typhimurium | | | | | | | | | |
| 40 mg | 83 a | 17 b | 83 a | 92 a | 17 b | 9 bc | 0 c | 0 c | 4.3 |
| 20 mg | 59 a | 0 b | 50 a | 50 a | 0 b | 0 b | 0 b | 0 b | 3 |
| 2 mg | 17 | 0 | 17 | 17 | 0 | 0 | 0 | 0 | 0 |
| S. Dublin | | | | | | | | | |
| 40 mg | 9 b | 9 bc | 42 a | 0 c | 0 c | 25 ab | 17 bc | 0 c | 5.9 |
| 20 mg | 0 c | 0 c | 33 a | 0 c | 0 c | 17 b | 9 bc | 0 c | 3 |
| 2 mg | 0 | 0 | 17 | 0 | 0 | 17 | 0 | 0 | 0 |
| S. enterica Entreritidis | | | | | | | | | |
| 40 mg | 9 bc | 0 c | 0 c | 0 c | 0 c | 17 b | 59 a | 0 c | 4.3 |
| 20 mg | 0 b | 0 b | 0 b | 0 b | 0 b | 17 b | 9 ab | 0 b | 3 |
| 2 mg | 0 | 0 | 0 | 0 | 0 | 0 | 0 | 0 | 0 |

TABLE 3-continued

Effect of Product Concentration on *Salmonella* Strain Agglutination

| | Lees Products | | | | Commercial Products | | | | |
|---|---|---|---|---|---|---|---|---|---|
| *Salmonella* Strain | CHC | PNC | CH1 | PN1 | CEL | SCP | OMN | INT | SEM |
| *S. enterica* Paratyphi B | | | | | | | | | |
| 40 mg | 33 a | 0 b | 0 b | 0 b | 0 b | 17 b | 33 a | 0 b | 8.3 |
| 20 mg | 0 | 0 | 0 | 0 | 0 | 17 | 0 | 0 | 0 |
| 2 mg | 0 | 0 | 0 | 0 | 0 | 0 | 0 | 0 | 0 |

S typhimurium: PN1, CH1 and CHC possessed a high degree of agglutination (92%, 83%, and 83% respectively) and substantially higher (P<0.001) than PNC, CEL and SCP (17%, 17%, and 9%, respectively, Table 3). OMN and INT exhibited no agglutination to this organism at 40 mg. At 20 mg, PN1, CH1 and CHC still maintained 50% agglutination, whereas the other products were 0 percent. These 3 products still sustained some agglutination potential (17%) at 2 mg.

S. Dublin: The highest agglutinations at 40 mg were with CH1 (42%), followed by SCP (25%), the remaining products were 17% or below. CH1 remained highest (33%) at the 20 mg level, followed by SCP (17%), with the remaining products at 9% and below. CH1 and SCP had 17% agglutination at 2 mg with the remainder at 0.

S. enterica Enteritidis: Omni was the only product that provided notable agglutination (59%) at the 40 mg level, while SCP provided 17%, and CHC 9%, with the remaining at 0%. OMN and SCP sustained a low % agglutination at 20 mg (9% and 17%, respectively). None of the products exhibited agglutination at 2 mg.

S. enterica Paratyphi B: CHC and OMN delivered similar and the highest (33%) agglutination at 40 mg, followed by SCP (17%), and 0% for the remainder. Only SCP maintained a small amount of agglutination (17%) at 20 mg, and no products demonstrated agglutination at 2 mg.

*Salmonella*

*Salmonella* typhimurium is a pathogenic gram-negative bacteria predominately found in the intestinal lumen. Its toxicity is due to an outer membrane consisting largely of lipopolysaccharides (LPS) which protect the bacteria from the environment (Tuin et. al. 2005). *Salmonella* typhimurium causes gastroenteritis in humans and other mammals. When the bacterial cells enter epithelial cells lining the intestine they cause host cell ruffling which temporarily damages the microvilli on the surface of the cell. This causes a rush of white blood cells into the mucosa, which throws off the ratios between absorption and secretion, and leads to diarrhea (McCormick et. al. 1995) In mice S. typhimurium causes symptoms resembling typhoid fever in humans Several outbreaks of this organism has occurred as a result of beef and poultry contamination. (Miao, et al 1999).

Of the products test CHC, CH1 and PN1 provided >80% agglutination of this organism. Whereas the highest agglutination provided by the commercial products was 17%, and 2 were 0% at the 40 mg dose.

As with *E. coli*, this does offer hope of attenuating the disease process through non-antibiotic means and could very well initiate the mounting for an immune response stimulating in innate and adaptive immune system against these organisms.

*Salmonella* Dublin can cause massive devastation to a herd and is transmissible to humans as well as other species. Frequently, this bacteria is antibiotic-resistant, making heightened biosecurity measures crucial to maintain herd health status: 75% of the strains showing ampicillin, ampicillin-sulbactam, ceftiofur, and/or tetracycline resistance. The bacteria are shed through feces and milk. Some animals may become lifetime carriers of the infection. With a 50% mortality rate, *Salmonella* Dublin can cause severe devastation. Stress—from overcrowding, poor air quality, co-infections, transportation, or nutritional deficiencies—can trigger the symptoms of this bacterial infection.

Since *Salmonella* Dublin is multi-drug resistant, it is a difficult infection to treat. Some antibiotics may treat secondary infections but the problem still remains. This residual bacteria may continue to be shed, infecting more herd mates. Providing sick calves with proper nutrition, ample water supply, and good air quality, gives the calves the best chance of survival.

Of the products tested, CH1 showed the highest numerical percentage of S. Dublin: 42%. As with *E. coli* O157:H7, the percentage agglutination was higher than any of the commercially products tested.

*Salmonella* Paratyphi B causes enteric fever in humans; the disease closely resembles Typhoid Fever, which is caused by the related serovar *Salmonella typhi*. *Salmonella Paratyphi* B multiplies in the gastrointestinal tract of humans, and then it penetrates the intestinal mucosa and is transferred via the lymph and the blood to deeper tissues such as the liver and spleen where it survives in macrophages.

This bacterium is host-specialized: grows well and causes disease only in humans, whereas most strains of *Salmonella* can grow in the gut of almost all animals, both domesticated and wild. Humans usually acquire *Salmonella* Paratyphi B by the ingestion of water or food that has been contaminated through fecal contact with humans. Most isolates of *Salmonella* belong to the species *S. enterica*. Paratyphi B is quite diverse and human infection is sometimes not associated with human to human system infection but rather associated with foodborne infection: some strains are susceptible to antibiotics, (Prager et al, 2003).

Relatively few of the products tested were effective in agglutinating *S enterica* Enteritidis or *S enterica* paratyphi B. OMN was most effective in agglutinating *S enterica* Enteritidis, Whereas CH1 and OMN were most effective in agglutinating S Paratyphi B. at the 40 mg level. Lower dose levels had relatively low or no agglutination for any of the product for these two bacterium.

Carbohydrate Concentrations

Carbohydrate concentrations in various compositions tested are presented in Table 4 and further summarized below:

TABLE 4

Carbohydrate composition in products

| (mg/mg) | Products | | | | | | SEM | P= |
|---|---|---|---|---|---|---|---|---|
| | CH1 | PN1 | GSR | CEL | SCP | OMN | | |
| Mannose | 0.056a | 0.037b | 0.018c | 0.018c | 0.056a | 0.018 | 0.003 | 0.01 |
| Galactose | 0 | 0 | 0 | 0.0215a | 0.014b | 0 | 0.002 | 0.01 |
| Glucose | 0.049b | 0.063b | 0.032b | 0.203a | 0.08ab | 0.023b | 0.030 | 0.01 |
| N-Acetyl Gal | NA | 0.098d | 0.594a | 0.301c | 0.363b | NA | 0.014 | 0.01 |

NA = Non detectable

Mannose concentration was highest in CH1 and SCP (0.056 mg/mg) and lowest for GSR, CEL and OMI (0.018 mg/mg). No galactose was detected in CH1, PN1 or GSR, while its concentration was highest in CEL, followed by SCP (0.0215 and 0.014 mg/mg respectively). Glucose concentration was highest in CEL compared to CH1, PN1, GSR and OMI with SCP not being different from any others. N-Acetyl galactosamine was highest (P<0.01) for SCP, followed by CEL, and PN1. CH1 and OMN showed no detectable levels of N-Acetyl galactosamine.

Figure 2:
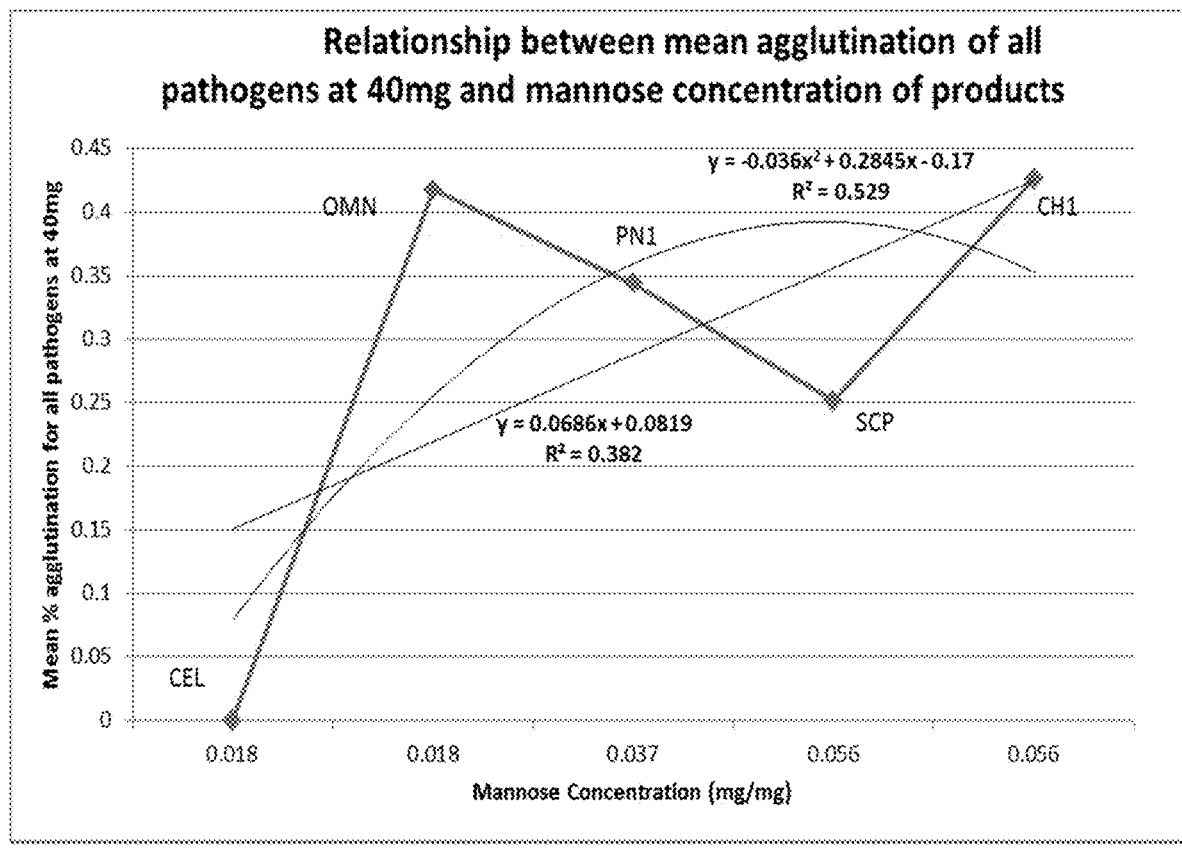
FIG. 2 is a graph of the effectiveness of preparations prepared in accordance with the present disclosure on bacterial agglutination, in comparison with the effectiveness of other preparations.

Yeast cell wall is composed of mannose complexes which have been linked to the degree of pathogen binding in the intestinal epithelium. Therefore, products containing high concentrations of mannose have been classified as products that would likely have a high probability of binding more pathogens. Lees products CH1 and commercial product SCP possessed the highest (0.056 mg/mg) concentration of mannose, and CEL and OMN lowest (0.018 mg/mg). The percentage of agglutination varied with bacterium and product. FIG. 2 shows the relationship of mannose concentration and mean 40 mg dose agglutination percentage across all organism for each product. The linear $r^2$ was 0.382. Only 5 products were represented (no agglutination trials were conducted with GSR), however, for CEL and OMN, of the 2 products with the lowest mannose concentration, CEL showed no agglutination, whereas OMN demonstrated the second highest agglutination percentage. On the other spectrum, products with the highest mannose concentration demonstrated the highest (CH1) and the second lowest (SCP) mean agglutination percentage. PN1 exhibited a moderate level of mannose and agglutination percentage. The specific mode of action associated with high agglutination is thus not explicable as a function of mannose concentration alone. The key facts remain that of the products and bacterium tested, CH1 and PN1 both exhibited agglutination percentages >80% for 3 organisms, and commercial products sold based on their pathogen agglutination efficacy revealed: OMN>80% for 2, SCP, >80% for 1, and CEL showed 0% agglutination for virtually all pathogens.

Bactericidal and Bacteriostatic Effects

Several preparations were also tested for their ability to prevent bacterial growth and/or to be bactericidal. In addition to PN1 and PN2 samples, prepared as described above, for some preparations grape skin residue (GSR) was included to determine whether components of GSR augment bacteriostatic or bactericidal activity of the lees preparations. GSR product was developed from grapes that were destemmed, macerated, and went through primary alcoholic fermentation. Upon completion of alcoholic fermentation, the must was pressed. The material remaining in the press was sampled and dried at 110° F. The following preparations were tested: PN1, PN2, GSR/PN1 (50:50 wt:wt) and GSR/CH1 (50:50, wt:wt), OMNI, and SCP.

Table 5 below shows the bacterial organisms against which bacteriostatic/bactericidal effects were tested.

TABLE 5

Organisms for bactericidal and bacteriostatic efficacy testing

| Bacteria Isolation | Isolation Source |
|---|---|
| Salmonella enterica ATCC 8759 | Gallbladder, Manteno, IL |
| Escherichia coli 0157:H7 ATCC 700728 | Not Available |
| Staphylococcus aureus ATCC 6538 | Human lesion |
| Bacillus cereus ATCC 11778 | Not Available |
| Listeria monocytogenes ATCC 19115 | Human |
| Streptococcus pyogenes ATCC 12384 | Not Available |
| Campylobacter jejuni ATCC 33291 | Human feces, Colorado |

The organisms were tested against the test articles at 4 different concentrations: 0 (control), 2, 20 and 40 mg/ml. CLSI standards M07-A10 were the guidelines for the study design of macro-broth dilution MICs.

Preparations of Inocula

Organisms were prepared individually from stock cultures and propagated according to manufacturer directions. Organisms were then sub-cultured onto appropriate media and incubated for a second pass at 37° C. for 24 hours. Stock solutions of each organism were made by adding colonies to 5 ml of 0.85% sterile saline and making adjustments as necessary to reach a suspension of approximately $1.5 \times 10^8$ cells/ml. One ml of each stock suspension was added to 149 ml of 0.85% sterile saline. This is a 1:150 dilution. One ml of the bacterial suspension was added to one ml of the test composition for a final bacterial concentration of approximately $5 \times 10^5$.

Preparing Test Compositions

Test compositions were re-hydrated in Mueller Hinton Broth. The test compositions were held at room temperature for 15 minutes and then vortexed until the test compositions dissolved. The test compositions were then centrifuged to pull any remaining particulates out of the solution. From this solution a 100 mg/ml stock solution was made. From the stock solution the three test solutions concentrations were made at 80, 40 and 4 mg/ml. When 1 ml of these concentrations were added to 1 ml of the bacterial inocula they were then at 40, 20 and 2 mg/ml.

Preparation and Inoculation of Samples

Sterile, 12×75 mm plastic test tubes were used to perform the test. 1 mL of the test compositions were placed in the appropriate labeled tubes. 1 mL of each adjusted bacterial inoculum was added to each appropriate labeled tube in the dilution series and mixed. The tubes were closed with loose caps. The tubes were then incubated at 37° C. for 24 hours with the exception of the Campylobacter tubes, which were incubated microaerophilically at 42° C. for 48 hours. At the end of the incubation phases the tubes were examined for turbidity. All optically clear tubes were plated to agar plates to determine if the test article was bactericidal or bacteriostatic. A product was considered to be "bactericidal" if less than 3 CFU were detected (Clear tubes with a few CFU), and "bacteriostatic" if greater the 3 CFU were detected (Clear tubes and growth detected).

The tubes were examined for turbidity, indicating growth of the organism. The organism grew in the growth control tube, and in any other tube that did not contain enough antimicrobial agent to inhibit growth. The lowest concentration of the agent that inhibits growth of the organism, as detected by lack of visual turbidity (matching the negative control) was designated the minimum inhibitory concentration (MIC).

The amount of growth in the tubes containing the test article was compared visually with the amount of growth in the growth-control tubes (no test article) used in each set of tests using the following scale: 1: optically clear; 2: slight increase (25%) in turbidity; 3: moderate increase (50%) in turbidity; 4: prominent increase (75%) in turbidity and 5, Turbid (=to control).

For quality control, a growth control tube containing Mueller Hinton without any test articles was used for each organism tested. This growth control also served as a turbidity control for reading end points. There was good growth in all of the growth control tubes for each organism. A sterility control tube (Blank) containing nothing but 1 mL of the Mueller Hinton solutions for each run was also tested. The sterility control was a "1" or optically clear.

Results:

Table 6 illustrates the results of product turbidity tests at three concentrations for each pathogen, as further summarized below.

TABLE 6

The effect of product concentration on growth of pathogenic bacteria

| Mg/ml | PN1 | PN2 | GSR/CH1 | GSR/PN1 | SCP | OMN | SEM | P= |
|---|---|---|---|---|---|---|---|---|
| | 2 | 2 | 2 | 2 | 2 | 2 | | |
| | | | Rep/Mean | | | | | |
| | | | Turbidity Reading[1] | | | | | |
| *Salmonella enterica* ATCC 8759 | | | | | | | | |
| 2 | 5 | 5 | 5 | 5 | 5 | 5 | —[3] | — |
| 20 | 4 | 3 | 4 | 5 | 5 | 5 | —[3] | — |
| 40 | $1^c$ | $2^{bc}$ | $3^b$ | $4.5^a$ | $5^a$ | $5^a$ | 0.20 | .001 |
| *Escherichia coli* 0157:H7 ATCC 700728 | | | | | | | | |
| 2 | 5 | 5 | 5 | 5 | 5 | 5 | — | — |
| 20 | 4 | 3 | 4 | 5 | 5 | 5 | — | — |
| 40 | $1^c$ | $2^{bc}$ | $3^b$ | $4^a$ | $5^a$ | $5^a$ | 0.21 | .001 |
| *Staphylococcus aureus* ATCC 6538 | | | | | | | | |
| 2 | 3 | 5 | 5 | 5 | 5 | 5 | — | — |
| 20 | $1.5^b$ | $2.5^{ab}$ | $3.5^{ab}$ | $3.5^{ab}$ | $5^a$ | $5^a$ | 0.54 | .019 |
| 40 | $1^b$ | $1^b$ | $2^{ab}$ | $3^{ab}$ | $5^a$ | $5^a$ | 0.58 | .007 |
| *Bacillus cereus* ATCC 11778 | | | | | | | | |
| 2 | 5 | 5 | 5 | 5 | 5 | 5 | — | — |
| 20 | $2^c$ | $2^c$ | $4^b$ | $5^a$ | $5^a$ | $5^a$ | 0.0017 | .001 |
| 40 | $1^c$ | $1^c$ | $1^c$ | $4^b$ | $5^a$ | $5^a$ | 0.0028 | .001 |
| *Listeria monocytogenes* ATCC 19115 | | | | | | | | |
| 2 | 5 | 5 | 5 | 5 | 5 | 5 | — | — |
| 20 | 3 | 3 | 5 | 5 | 5 | 5 | 0.41 | .02 |
| 40 | $1^b$ | $1^b$ | $3^{ab}$ | $4^a$ | $5^a$ | $5^a$ | 0.31 | .001 |
| *Streptococcus pyogenes* ATCC 12384 | | | | | | | | |
| 2 | 4 | 5 | 5 | 5 | 5 | 5 | — | — |
| 20 | $4^{ab}$ | $2.5^b$ | $5^a$ | $5^a$ | $5^a$ | $5^a$ | 0.46 | .038 |
| 40 | $1^b$ | $1^b$ | $1^b$ | $4^a$ | $5^a$ | $5^a$ | 0.20 | .001 |
| *Campylobacter jejuni* ATCC 33291 | | | | | | | | |
| 2 | 5 | 5 | 5 | 5 | 5 | 5 | — | — |
| 20 | 5 | 5 | 5 | 5 | 5 | 5 | — | — |
| 40 | 5 | 5 | 5 | 5 | 5 | 5 | — | — |

[1] 1: optically clear; 2: slight increase (25%) in turbidity; 3: moderate increase (50%) in turbidity; 4: prominent increase (75%) in turbidity and 5 turbid (=to control).
[2] Means in the same row whose superscripts do not share a common letter differ from each other with a statistical significance of $p < 0.05$ by Tukey-Kramer mean separation test.
[3] No variation in replicates or treatments was detected.

Two mg/ml had no effect on reducing growth for any pathogens. In addition, the two commercial products demonstrated no reduction in growth compared to control for any microorganism at any concentration.

*Salmonella enterica* and *E. coli* 0157:H7 showed the same response to products and product concentration. At 20 mg/ml, PN1, PN2 and GSR/CH1 slightly reduced growth, although not significantly (p>0.05). At 40 mg/ml, PN1 demonstrated no growth present for both pathogens, while PN2 and GSR/CH1 showed slight and moderate growth respectively. The addition of GSR reduced the effectiveness of PN1 (essentially had no effect: since GSR was included at 50%, the concentration of PN1 was 20 mg/ml at the 40 mg/ml inclusion). The commercial products had no effect on turbidity.

PN1 significantly reduced (p<0.05) the turbidity of Staphylococcus aureus at 20 mg/ml compared to SCP and Omni, with PN2, GSR/PN1 and GSR/CH1 not being different than either. At 40 mg/ml, both PN1 and PN2 showed no growth and had significantly lower (p<0.05) scores than SCP and OMN. Although GSR/PN1 and GSR/CH1 showed only slight and moderate growth, they were not different than either.

Bacillus cereus showed a distinct lineation in growth among products at 20 mg/ml, with PN1 and PN2 being less (p<0.05) turbid than GSR/CH1 and the latter being less turbid than the commercial products (SCP and Omni). At 40 mg/ml, this microorganism showed a score of "1" for PN1, PN2 and GSR/CH1, which was lower (p<0.05) than GSR/PN1, which was lower (p<0.05) than Omni and SCP. For this organism, it appeared that the addition of GSR was impairing the effectiveness of PN1, since PN1 showed a score of "2" without GSR at 20 mg/ml and a score of "4" with the same concentration and the addition of GSR at 40 mg/ml.

Growth of Listeria monocytogenes was reduced (p<0.05) by PN1 and PN2 at 20 mg/ml compared to other products. At 40 mg/ml, PN1 and PN2 were clear and lower (P=0.05) than GSR/PN1, OMN and SCP, with GSR/CH1 not being different than either. For Streptococcus pyogenes, growth was reduced (p<0.05) at the 20 mg/ml concentration for PN2 compared the GSR/PN1, GSR/CH1, Omni and SCP, with PN1 not being different from either. Three products inhibited growth entirely (clear, score=1) for this organism at 40 m/ml:PN1, PN2 and GSR/CH1, compared (p<0.05) to the remaining treatments which had no effect on reducing turbidity. None of the products at any concentration had an effect on Campylobacter jejuni growth.

Table 7 summarizes the products and microorganisms with a turbidity score equal to "1". These products qualified for subsequent plating to determine if the effect of these products was "static" or "cidal" on growth. Only the 40 mg/ml concentration of PN1, PN2 and GSR/CH1 showed clear tubes (score=1).

TABLE 7

Bactericidal and bacteriostatic checks on optically clear tubes

| Organism | Test product | | |
| --- | --- | --- | --- |
| | PN1 | PN2 | GSR/CH1 |
| Salmonella enterica ATCC 8759 | TNTC[2] | — | — |
| E. coli 0157:H7 ATCC 700728 | TNTC | — | — |
| Staphylococcus aureus ATCC 6538 | TNTC | TNTC | — |
| Bacillus cereus ATCC 11778 | 1[3] | 1 | TNTC |
| Listeria monocytogenes ATCC 19115 | TNTC | TNTC | — |
| Streptococcus pyogenes ATCC 12384 | 2 | 2 | 0 |

[1]All above are plated from optically clear (Turbidity score = 1) tubes at 40 mg/ml.
[2]TNTC = Too numerous to count
[3]Numbers represent CFU/ml Salmonella enterica and E. coli 0157:H7 with PN1, Staphylococcus aureus and Listeria monocytogenes PN1 and PN2 and Bacillus cereus for CSR/CH1 all showed plates counts "To Numerous To Count" (TNTC) which indicates that reduced turbidity had been due to growth inhibition (i.e., bacteriostatic effect), rather than a bactericidal effect. Bacillus cereus for PN1 and PN2 and Streptococcus pyogenes for PN1, PN2 and GSR/CH1 all showed less than 3 CFU when plated, strongly suggesting a "bactericidal" action of these products on these specific microorganisms. It is very likely however, that a dose less than 40 but greater than 20 mg/ml would have yielded scores equal to 1 for these products.

The exposure of 20 mg/ml of PN1 and/or PN2 reduced the growth of S. aureus, B. cereus, L. monocytogenes and S. pyogenes. The exposure of 40 mg/ml of PN1, PN2 and/or CSR/CH1 reduced the growth of S. aureus, B. cereus, L. monocytogenes and S. pyogenes. No commercial products had an effect on reducing growth of any of the pathogenic organisms. Grape skin residue (GSR) had no associative and/or positive effects on microorganism growth when combined with lees from PN. None of the products had an effect on growth of Campylobacter jejuni. The Minimum Inhibitory Concentration (MIC) for PN1, PN2 and GSR/CH1 is most likely less than 40 but greater than 20 mg/ml. Bacteriostatic effects on microbial growth were shown for the following microorganism and products: Salmonella enterica and E. coli 0157:H7 with PN1, Staphylococcus aureus and Listeria monocytogenes PN1 and PN2 and Bacillus cereus for CSR/CH1. Bactericidal effects on microbial growth were shown for the following microorganism and products: Bacillus cereus for PN1 and PN2 and Streptococcus pyogenes for PN1, PN2 and GSR/CH1

Effects of aging preparation, elevated drying temperature, and effectiveness of YCW preparations from beer brewing residue on agglutination In a further experiment, effects of time of storage of dried lees, effects of different lees drying temperatures, further comparisons of enzyme treatment of lees, and preparations made from yeast residue following fermentation during brewing beer were tested for their agglutination ability against E. coli 0157:H7 (ATCC 700728) and Salmonella typhimurium (ATCC 14028). Methods were as described above for testing agglutination except that E. coli 0157:H7 and Salmonella typhimurium were suspended at a higher concentration, of approximately $3.3 \times 10^9$ and $3.3 \times 10^9$, respectively, and the following preparations were used in the creation of test preparations as described:

A lees preparation from Pinot Noir grapes that had not been enzymatically treated and had been prepared approximately 14 months before testing (PNC15), a lees preparation from Pinot Noir grapes that had not been enzymatically treated and had been prepared approximately 2 months before testing (PNC16), a lees preparation from Pinot Noir grapes that had been enzymatically treated and had been prepared approximately 2 months before testing (PNC16), a lees preparation from Pinot Noir grapes that had not been enzymatically treated, had been prepared approximately 2 months before testing, and was dried at 170° F. instead of 120° F. (PNHT16); a lees preparation from Cabernet Franc grapes that had not been enzymatically treated and had been prepared approximately 2 months before testing (CFC16); a lees preparation from Cabernet Franc grapes that had not been enzymatically treated and had been prepared approximately 2 months before testing (CFE16), a preparation made from the slurry remaining at the bottom of a fermentation tank during beer brewing (referred to herein as "beer lees" also known as trub) not treated enzymatically (BLC), a preparation made from beer lees and treated with enzymes (BLE), and CELMANAX™ (SCP) (hydrolyzed yeast).

TABLE 8

Effect of yeast cell wall and commercial yeast extract product concentration on agglutination activity of pathogenic bacteria

| Conc | Treatments | | | | | | | | | | |
|---|---|---|---|---|---|---|---|---|---|---|---|
|  | PNC15 | PNC16 | PNE16 | PNHT16 | CFC16 | CFE16 | BLC | BLE | SCP | SE | P |
| *Salmonella*, % agglutination | | | | | | | | | | | |
| 40 mg/ml | 67$^b$ | 83$^a$ | 58.5$^{bc}$ | 50$^c$ | 67$^b$ | 83$^a$ | 67$^b$ | 67$^b$ | 67$^b$ | 2.8 | .001 |
| 20 mg/ml | 50$^b$ | 67$^a$ | 50$^b$ | 50$^b$ | 17$^c$ | 75$^a$ | 67$^a$ | 67$^a$ | 50$^b$ | 2.7 | .001 |
| *Escherichia coli* 0157:H7, % agglutination | | | | | | | | | | | |
| 40 mg/ml | 75$^{ab}$ | 84$^{ab}$ | 17$^{cd}$ | 50$^{bc}$ | 83$^{ab}$ | 92$^a$ | 0$^d$ | 17$^{cd}$ | 0$^d$ | 6.7 | .001 |
| 20 mg/ml | 0$^c$ | 17$^b$ | 0$^c$ | 0$^c$ | 42$^a$ | 17$^b$ | 0$^c$ | 0$^c$ | 0$^c$ | 2.8 | .001 |

SE is standard error. Means in the same row whose superscripts do not share a common letter differ from each other with a statistical significance of (p<0.05) by Tukey-Kramer mean separation test.

Results shown in Table 8 can be summarized as follows. For *Salmonella* typhimurium (ST), at 40 gm/ml, PNC16 and CFE16 demonstrated the highest (p<0.05) level of agglutination against ST. Although the lowest agglutination was at 40 mg/ml for ST was PNHT16, it was still 50%, and not different from PNE16, suggesting that whereas a lees-drying temperature of 120° F. yielded high agglutination, a higher lees-drying temperature (170° F.) may have a denaturing effect on the product and somewhat reduce its agglutination ability. The effect of increased drying temperature resulted in a reduction of agglutination activity (83 vs 50 for 40 mg/ml and 67 vs 50% for 20 mg/ml for PN15 and PNC16 respectively. The remaining products (PNC15, PNE16, CFC16, BLC, BLE and SCP) were intermediate, ranging from 58.5 to 67% agglutination. Generally, reducing the concentration of product to 20 mg/ml reduced agglutination by about 15 percentage units for PN15, PNC16, CFE16 and SCP. PNHT16, BLC and BLE agglutinated the same at 20 and 40 mg/ml. At both concentrations PNC15 continued to exhibit high agglutination levels, indicating only a slight (approximately 17%) reduction in agglutination activity with time. The addition of enzyme had a positive effect on the agglutination activity Cabernet Franc, no effect on beer lees and a negative on Pinot Noir. Although a slight elevation for CFE16 and PNC16, grape and beer sources of lees had similar agglutination activity for ST at 40 mg/ml.

For *E. Coli* 0157: H7 (EC), PNC15, PNC16, CFC16 and CFE16 demonstrated higher (p<0.05) agglutination activity than BLE, PNE16, BLC and SCP at 40 mg/ml for EC. Shelf life did not affect agglutination activity for PN. Increasing drying temperature (PNHT16) resulted in an agglutination activity that was numerically but not statistically different the PNC16. (Drying temperature of 120° F. was used for all subsequent preparations.) The addition of enzyme decreased agglutination activity for PN, and did not affect CF or BL. At the 20 mg/ml concentration, only 3 products demonstrated any agglutination activity for EC, with the highest being CFC16 at 41.5%. Significantly, however, the commercial product SCP showed no agglutination activity at either concentration for EC, indicating improved effectiveness of using the wine and beer lees based compositions disclosed herein over conventional products. For both pathogens and concentrations, CFE16, PNC16, CFC16, PNC15 and BLE had the highest and SCP the lowest agglutination activity.

Surprisingly, lees source agglutination activity was affected differently by enzyme addition. For Cabernet Franc lees, enzyme addition increased agglutination activity, for Pinot Noir enzyme addition reduced agglutination activity, and for beer lees, enzyme addition had no effect.

Further Examples of Bactericidal and Bacteriostatic Effects

Additional experiments were performed to determine bactericidal and bacteriostatic effects of preparation made from wine lees from different varietals, effects of aging of preparations on bactericidal and bacteriostatic effectiveness, and to compare effectiveness to conventional antibiotic treatment. Methods were as described above for testing bacteriostatic and bactericidal effects. Preparations were tested against *Salmonella enterica* (ATCC 8759) and *E. coli* 0157:H7 (ATCC 700728).

The following preparations were tested: a lees preparation from Chardonnay grapes that had not been enzymatically treated and had been prepared approximately 2 months before testing (CH16), a lees preparation from Pinot Noir grapes that had not been enzymatically treated and had been prepared approximately 14 months before testing (PNC15), a lees preparation from Pinot Noir grapes that had not been enzymatically treated and had been prepared approximately 2 months before testing (PNC16), a lees preparation from Cabernet Franc grapes that had been enzymatically treated and had been prepared approximately 2 months before testing (CFE16), CELMANAX™ (SCP) (hydrolyzed yeast), and salinomycin, 0.005% solution (antibiotic).

Minimal inhibitory concentration results are shown in Table 9:

TABLE 9

Minimal Inhibitory Concentration test article/concentration on growth of pathogenic bacteria

| Mg/ml | Control | CH1 | PNC15 | PNC16 | CFE16 | SCP | ABX | SEM | P= |
|---|---|---|---|---|---|---|---|---|---|
| | 2 | 2 | 2 | 2 | 2 | 2 | 2 | | |
| | Rep/Mean | | | | | | | | |
| | Turbidity Reading (OD) | | | | | | | | |
| *Salmonella enterica* ATCC 8759 | | | | | | | | | |
| 40 | .506$^a$ | .021$^c$ | .013$^c$ | .001$^c$ | .025$^c$ | .166$^b$ | .004$^c$ | .009 | .01 |
| 20 | .506$^a$ | .186$^b$ | .085$^{cd}$ | .115$^{bc}$ | .484$^a$ | .468$^a$ | .004$^d$ | .017 | .01 |
| *Escherichia coli* 0157:H7 ATCC 700728 | | | | | | | | | |
| 40 | .525$^a$ | .021$^d$ | .001$^e$ | .006$^{de}$ | .001$^e$ | .185$^b$ | .075$^c$ | .003 | .01 |
| 20 | .525$^a$ | .004$^{de}$ | .001$^e$ | .034$^d$ | .444$^a$ | .550$^a$ | .075$^c$ | .006 | .01 |

SEM is standard error of the mean. Means in the same row whose superscripts do not share a common letter differ from each other with a statistical significance of (p < 0.05) by Tukey-Kramer mean separation test. Optically clear = 0.0 OD As for *Salmonella enterica*:

At 40 mg/ml, the OD for the SCP (commercial product) was higher (p<0.01) than all other lees test articles, indicating less growth inhibition by SCP than by preparations disclosed herein. All lees test articles were equal in growth inhibition compared to each other and to the ABX treatment. PNC16 showed numerically greater growth inhibition than ABX, although this difference did not attain statistical significance.

When the dose was halved (20 mg/ml), the OD for SCP and CFE16 were not different from Control, but all three were higher (P<0.01) than the remaining treatments. CH1 was higher in OD than PNC15 and ABX but not different from PNC16. The OD of PNC15 was not different from ABX, indicating an equal effectiveness in reducing growth of *S. enterica*.

As for *E. coli* 0157:H7

All test article OD readings were lower (p<0.05) than Control at the 40 mg/ml dose. SCP was higher (p<0.05) than the ABX, with all lees treatments being lower (p<0.05) than ABX, suggesting the lees treatments were more effective in controlling growth of *E. coli*. CH1 and PNC16 were similar in OD. CH1 was higher than CFE16 and PNC15.

At the 20 mg/ml, as with *S. enterica*, the OD for SCP was similar to Control, indicating ineffectiveness at this concentration of conventional products. By comparison, all lees treatments (PNC16, CH1 and PNC15) except CFE16 were lower at a statistically significant level (p<0.05) in OD than ABX (and SCP) indicating superior bacteriostatic effects of the lees-based preparations disclosed herein compared to antibiotic or conventional products.

Table 10 summarizes bactericidal and bacteriostatic checks on optically clear tubes

TABLE 10

Bactericidal[1] or Static checks of optically clear tubes from the MIC evaluation (CFU/ml)

| Mg/ml | Control | CH1 | PNC15 | PNC16 | CFE16 | SCP | ABX |
|---|---|---|---|---|---|---|---|
| | 2 | 2 | 2 | 2 | 2 | 2 | 2 |
| | Rep/Mean | | | | | | |
| | CFU/ml | | | | | | |
| *Salmonella enterica* ATCC 8759 | | | | | | | |
| 40 | | 25,000 | 25,000 | 16,000 | MG/NA[1] | MG/NA | 50,000 |
| 20 | | MG/NA | MG/NA | MG/NA | MG/NA | MG/NA | 50,000 |
| *Escherichia coli* 0157:H7 ATCC 700728 | | | | | | | |
| 40 | | 100 | 2,800 | 50 | 17,000 | MG/NA | 950 |
| 20 | | 3,500 | 14,000 | 16,000 | MG/NA | MG/NA | 950 |

MG/NA = Microbial growth (OD > 0) in the MIC tubes therefore not applicable to the bactericidal/static evaluation.
[1]A "0 CFU/ml" reading was needed in order to qualify as "bactericidal"

As shown in Table 10, at the 40 mg/ml dose for *S. enterica*, CH1, PNC15, PNC16 and ABX demonstrated optical clarity (< . . . 0 OD for the MIC evaluation), however they all grew the pathogens during bactericidal/static evaluation, indicating a bacteriostatic rather than bactericidal activity. The ABX treatment exhibited two-fold more growth than lees treatments disclosed herein. CFE16 and SCP exhibited microbial growth (high OD) during the MIC test, therefore did not qualify for the bactericidal/static evaluation. When dosed at 20 mg/ml, all test articles exhibited microbial growth during the MIC test, therefore did not qualify for the bactericidal/static evaluation.

For *E coli* with product dosage at 40 mg/ml, CH1 and PNC16 produced 100 or less CFU/ml, although not 0, the low CFU count suggests these products are approaching being bactericidal effectiveness. PNC15, CFE16 and ABX at 2,800, 17,000 and 950 CFU/ml were in the static category. SCP did not qualify for the bactericidal/static evaluation because of its OD for the MIC. At 20 mg/ml, 3 of the 4 lees treatments remained clear and CH1, PNC15 and PNC16 grew 3,500, 14,000 and 16,000, respectively. SCP and CHE16 had high OD readings during the MIC and therefore did not qualify for the bactericidal/static evaluation.

Thus, for *Salmonella enterica*, the lees preparations as disclosed herein at 40 mg/ml were as effective as Salinomycin in controlling growth, with conventional commercially product being less effective than any other tested. At the 20 mg/ml dose, SCP and CFE16 were not effective in reducing pathogenic growth and were similar to Control.

The remaining test articles were more effective (lower OD), and PNC15 remained as effective as Salinomycin. For *E. coli* at 40 mg/ml, conventional commercially available product was less effective in controlling growth than the ABX, with all lees test articles showing greater inhibition of bacterial growth than ABX. All lees test articles, except CFE16, were more effective than Salinomycin in controlling growth. For both pathogens, the commercial product (SCP) was not effective in controlling growth at the lower dosage level (20 mg/ml). The Minimum Inhibitory Concentration (MIC) for lees treatments is most likely between 20 mg/ml and 40 mg/ml.

In vivo testing for health effects of lees-based preparations in cow calves

An in vivo study was performed to compare effects of lees-based preparations as disclosed herein to conventional commercially available product yeast fermentation product and Decoquinate on performance and health of neonatal Holstein calves. Lees was prepared as described above (a lees preparation from Pinot Noir grapes that had not been enzymatically treated and had been prepared approximately 6 months before testing (PNC16)). PNC16 was compared with CELMANAX™ (SCP) (hydrolyzed yeast) and an antibiotic, DECCOX®-M manufactured by Zoetis Inc., Decoquinate.

The study was conducted at Spruce Haven Farms, Union Springs, N.Y., a commercial dairy consisting of 1,800 mature cows. There were thirty calf hutches available to conduct the trial that were aligned in one row. The study consisted of thirty female Holstein calves. As calves were born they were successively placed on one of four treatments until 28 calves were assigned, then the remaining 2 calves were assigned to treatment 2 and 3 respectively. The treatments were as follows: Control (no test article), SCP (10 ml of liquid hydrolyzed yeast, CELMANAX™, dissolved in the milk during the morning feeding), PNC16 (10 ml of a liquid pinot noir lees preparation dissolved in the milk during the morning feeding), and DECCOX® dissolved in the milk at a rate of 22.7 mg/45.4 kg of body weight.

Calves were housed in fiberglass hutches (4'×8') with an outside run (4'×6') with straw bedding inside the hutch. Within 2 hr. of birth, calves were offered 4 lb. of colostrum. Thereafter, pasteurized whole milk was offered twice daily (08:00 and 16:00 h) and water and dry calf starter was available at all times in removable buckets. During the morning feeding the liquid (CEL or PNC16) or dry (22.7 mg) test articles were dissolved in the milk. Calves body weights were recorded when moved into the hutches and again at 21 d of life.

Blood samples were collected via jugular vein-puncture before the pm milk feeding on day 10 of life. Samples were collected in heparinized vacutainers. Whole blood was analyzed for hematology: red blood count, hematocrit, hemoglobin, mean cell volume, mean cell hemoglobin, mean cell hemoglobin concentration, red cell distribution width, reticulocyte, white blood cell: neutrophil, lymphocyte, monocyte, eosinophil, basophil, platelet, mean platelet volume, platelet, distribution width and procalcitonin. Plasma was obtained by centrifugation at 1,500×g for 15 min. Plasma samples were frozen (−40° C.) and shipped to the Michigan State University (DCPAH) laboratory for haptoglobin analysis.

Fecal samples (~10-20 g) were obtain via digital stimulation from each calf on day 7, 14 and 21 of life. Samples were sent to the Cornell Diagnostic Laboratory for zinc sulfate floatation to determine type and degree of fecal shedding. Body temperatures were take just prior to fecal collections on day 7, 14 and 21 of life. Fecal consistency scores: were recorded for each calf daily using the following scale: 1=soft, solid consistency, no fluid, 2=semi-solid, mostly solid, 3=runny: semi solid, mostly fluid, 4=watery, all fluid 5=watery with blood.

Statistical analysis was by One-way ANOV using SAS JMP. When a time component was involved: temperature, fecal consistency score, fecal shedding, the model was: test article (TA)+Time+TA×Time. A significant (p<0.01) interaction between time and TA was present for fecal consistency score and fecal shedding, thus a one-way ANOV was conducted at each time.

As shown in Table 11, weight gain was not affected by treatment, however, there was a tendency (p=0.10) for PNC16 calves to gain more than Control calves with other test articles not different from either (Table 1). Average daily gain was low, as is typical in the few weeks of life, and reflected weight gain.

TABLE 11

Effect of test article on body weight gain in Holstein calves from birth through day 21

| | Test Article | | | | | |
|---|---|---|---|---|---|---|
| | Control | CEL | PNC16 | DECCOX ® | SEM | P= |
| Birth wt, kg | 40.4 | 40.7 | 41.1 | 40.2 | .27 | .18 |
| Day 21 wt, kg | 47.1$^b$ | 48.7$^{ab}$ | 49.8$^a$ | 47.6$^b$ | .53 | .01 |
| Body wt gain, kg | 6.8 | 8.0 | 8.7 | 7.3 | .54 | .10 |
| ADG, kg/d | .32 | .38 | .42 | .35 | .03 | .10 |

Hematology data is should in table 12.

TABLE 12

Effect of test article on hematology and haptoglobin concentration in 10 day old Holstein calves.

| | | | Test Article | | | | | |
|---|---|---|---|---|---|---|---|---|
| Item | Abrev | Units | Control | SCP | PNC16 | DECCOX ® | SEM | P= |
| Red Blood Count | RBC | M/uL | 7.4 | 8.2 | 8.3 | 7.1 | 1.40 | 0.33 |
| Hematocrit | HCT | % | 29.8 | 33.0 | 33.0 | 28.5 | 6.80 | 0.51 |
| Hemoglobin | HBG | g/dL | 9.4 | 10.2 | 10.2 | 8.9 | 1.90 | 0.51 |
| Mean Cell Volume | MCV | fL | 40.0 | 40.0 | 39.7 | 39.8 | 2.30 | 0.98 |
| Mean Cell Hemoglobin | MCH | pg | 12.6 | 12.4 | 12.3 | 12.4 | 0.42 | 0.64 |
| Mean Cell Hemoglobin Concentration | MCHC | g/dL | 31.5 | 31.0 | 31.1 | 31.4 | 1.23 | 0.78 |
| Red Cell Distribution Width | RDW | % | 31.4 | 33.0 | 32.8 | 30.7 | 2.60 | 0.33 |

TABLE 12-continued

Effect of test article on hematology and haptoglobin concentration in 10 day old Holstein calves.

| Item | Abrev | Units | Control | SCP | PNC16 | DECCOX ® | SEM | P= |
|---|---|---|---|---|---|---|---|---|
| Reticulocyte | Ret | K/ul | 7.13$^a$ | 1.98$^b$ | 0.89$^b$ | 1.49$^b$ | 2.56 | 0.02 |
| White Blood Cell | WBC | K/ul | 7.96$^b$ | 10.59$^a$ | 11.51$^a$ | 7.67$^b$ | 2.50 | 0.04 |
| Neutrophil | NEUT | K/ul | 3.7 | 6.0 | 7.0 | 5.1 | 2.41 | 0.06 |
| Lymphocyte | LYMPH | K/ul | 4.2 | 4.5 | 4.4 | 2.4 | 1.36 | 0.09 |
| Monocyte | Mono | K/ul | 0.02 | 0.03 | 0.02 | 0.05 | 0.04 | 0.44 |
| Eosinophil | Eosin | K/ul | 0.03 | 0.06 | 0.10 | 0.08 | 0.06 | 0.27 |
| Basophil | Baso | K/ul | 0.01 | 0.02 | 0.01 | 0.00 | 0.01 | 0.35 |
| Neutrophil/Lymphocyte Ratio | NLR | | .87$^b$ | 1.33$^{ab}$ | 1.59$^{ab}$ | 2.11$^a$ | .28 | 0.03 |
| Percentages | Neutrophil | % | 48.38$^b$ | 55.05$^{ab}$ | 59.38$^{ab}$ | 66.63$^a$ | 8.96 | 0.07 |
| | Lymphocyte | % | 50.87$^a$ | 43.99$^{ab}$ | 39.4$^{ab}$ | 31.75$^b$ | 8.50 | 0.02 |
| | Mono | % | 0.21 | 0.26 | 0.18 | 0.63 | 0.32 | 0.37 |
| | Eosin | % | 0.34 | 0.53 | 0.94 | 0.98 | 0.74 | 0.30 |
| | Baso | % | 0.19 | 0.18 | 0.08 | 0.00 | 0.23 | 0.53 |
| | Total | | 100 | 100 | 100 | 100 | | |
| Platelet | Plt | K/ul | 654.7$^{ab}$ | 847.8$^{ab}$ | 905.1$^a$ | 579.8$^b$ | 183.0 | 0.01 |
| Mean Platelet Volume | MPV | fL | 5.5 | 5.1 | 6.3 | 5.6 | 0.95 | 0.16 |
| Platelet Distribution Width | PDW | fL | 6.34$^b$ | 7.4$^{ab}$ | 7.71$^a$ | 7.72$^a$ | 0.83 | 0.02 |
| Procalcitonin | PCT | % | 0.35$^b$ | 0.42$^{ab}$ | 0.53$^a$ | 0.33$^b$ | 1.05 | 0.01 |
| Haptoglobin ug/ml | Hp | ug/ml | 24.13 | 38.2 | 22.7 | 64.5 | 26.8 | 0.72 |

The only red cell parameter that demonstrated a difference was reticulocyte concentration, with Control calves being higher (0.05) than calves receiving other test articles. All other RBC parameters were not affected by test article. Reticulocytes are immature RBC and remain in the blood for about 2 days before developing into mature red blood cells. A high reticulocyte count suggests the bone marrow is being directed to manufacture more RBC because of some demand: for example, internal bleeding. No bloody feces were observed for this treatment.

White blood cells were highest (p<0.05) for SCP and PNC16 compared to other test articles. Neutrophil concentration tended (p=0.057) to be higher for PNC16 compared to Control, with other test articles not being different from these. However, neutrophils, as a percent of total cells were higher (p=0.05) for DECCOX® than Control, with SCP and PNC16 not being different from either. There was a tendency for lymphocyte concentration to be lower (P=0.091) for DECCOX® than other test articles, however, the percent of cells as lymphocytes was lowest for DECCOX® compared to Control with SCP and PNC16 not being different from either.

The Neutrophil: Lymphocyte ratio (NLR) therefore was higher (p=0.05) for DECCOX® compared to Control, with SCP and PNC16 not being different from either. Neutrophils and Lymphocytes are first responders to a bacterial infection and acute inflammation therefore relative elevation in concentration suggests some predominance of a bacterial infection and/or inflammation. For neutrophils, the test articles were similar and elevated compared to the Control, however, the DECCOX® was lower in lymphocytes compared to other test articles. The higher NLR for test articles compared to Control suggest they may either be responding to or creating an inflammatory environment.

Platelet count was higher (p=0.05) for PNC16 compared to DECCOX® with Control and SCP not being different from either. PDW was elevated for PNC16 and DECCOX® compared to Control with SCP not being different from either. Procalcitonin was higher for PNC16 compared to Control and DECCOX® with SCP not being different from either. Mild to moderately elevated platelet counts are commonly seen when chronic inflammation is present. A high PDW means that platelet size varies greatly, an indication that there may be a disorder affecting platelet production. Biomarkers like procalcitonin (PCT) are considered useful as an indication of bacterial infection and sepsis and/or a systemic inflammatory response.

Mean haptoglobin concentrations in the present trial ranged from 22.7 (PNC16) to 64.5 ug/ml (DECCOX®), although the variation within test article was high (SD=26.8). Although haptoglobin numerical means followed trends associated with temperatures and fecal consistency scores, they were not significant. Haptoglobin is primarily produced in the liver and binds hemoglobin which prevents utilization of iron by bacteria translocated into blood (Wassell 2000). Because haptoglobin levels become depleted in the presence of large amounts of free hemoglobin, decreased haptoglobin is also a marker of hemolysis. (Shih et al 2014). Haptoglobin also acts as an antioxidant, has antibacterial activity and plays a role in modulating many aspects of the acute phase immune response. (Wassell 2000). Acute phase proteins such as SAA, haptoglobin, and CGRP are also secreted by hepatocytes during inflammatory conditions in response to proinflammatory cytokines. Thus, when elevated could potentially indicate the presence of an inflammation or the development of an inflammatory process. Harris et al 2017 fed yeast fermented products to calves that were challenged with *Salmonella* Typhimurium from birth to 35 d. They observed no difference in haptoglobin concentration, with mean serum concentrations ranging 48.8 to 63 ug/ml, with extreme variation in calves (SEM=31.68). Alsemgeest et al 1994 concluded that the plasma haptoglobin is a useful parameter to distinguish healthy animals from animals with inflammation and can be helpful in distinguishing between acute and chronic of inflammatory diseases.

Temperatures:

Rectal temperatures at 7 and 21 d of life were similar among test articles. On day 14, temperatures for calves receiving DECCOX® were higher (p<005) than PNC16, with SCP and Control not being different than either.

Fecal Consistency Scores (FCS):

Overall (day 1-21) mean FCS was higher (p>0.05) for SCP compared to Control and DECCOX®, with PNC16 not being different from either. Mean FCS was between 2 and 2.5 from birth to 11 days of age. The critical window of difference appeared to be between day 12 and 17 d of life. All FCS were elevated, however, SCP and PNC16 were higher (p=0.05, 3.0 and 2.8 respectively) compared to Control and DECCOX® (2.3 and 2.4, respectively). Mean FCS score returned to pre- 12-day levels after day 17. No deliberate nutritional changes occurred during this 21 d trial period, therefore it would appear that any increase FSC may be associated with a physiological response to an enteric irritant and corroborates with the elevated temperature.

Fecal Shedding:

Day 1 of life, no calves were shedding *Cryptosporidium* oocytes (Table 13).

TABLE 13

Effect of test articles on fecal shedding of *Cryptosporidium* oocytes in Holstein calves

| | Test Articles | | | | | |
|---|---|---|---|---|---|---|
| Day | Control | SCP | PNC16 | DECCOX® | SEM | P= |
| | Oocytes/g of feces | | | | | |
| 1 | 0 | 0 | 0 | 0 | 0 | 0 |
| 7 | 85638$^a$ | 4499$^b$ | 1226$^b$ | 2$^b$ | 26631 | 0.079 |
| 14 | 14153$^{ab}$ | 8229$^b$ | 31661$^{ab}$ | 209473$^a$ | 51245 | 0.034 |
| 21 | 368$^a$ | 0$^b$ | 0$^b$ | 11$^b$ | 109 | 0.073 |
| | % of calves shedding | | | | | |
| 1 | 0.0 | 0.0 | 0.0 | 0.0 | | |
| 7 | 71.4 | 50.0 | 37.5 | 28.6 | | |
| 14 | 85.0 | 87.5 | 87.5 | 100.0 | | |
| 21 | 28.6 | 0.0 | 0.0 | 28.6 | | |

On day 7, there was a tendency (p=0.079) for Control calves to be shedding more oocytes than those on SCP, PNC16 or DECCOX®. Day 14 showed calves consuming DECCOX® were shedding more oocytes than calves fed CEL, with Control and PNC16 not being different from either. By day 21, shedding was very low, but tended to be higher (p=0.07) for Control calves than those on other test articles. Percent calves shedding on day 7 highest for Control (71.4%) and lowest for PNC16 (37.5%) and DECCOX® (28.6%). By day 14, greater than 85% of all calves were shedding. By day 21, no calves on CEL or PNC16 were shedding, and only 28.6% on Control and DECCOX®.

Figure 3:
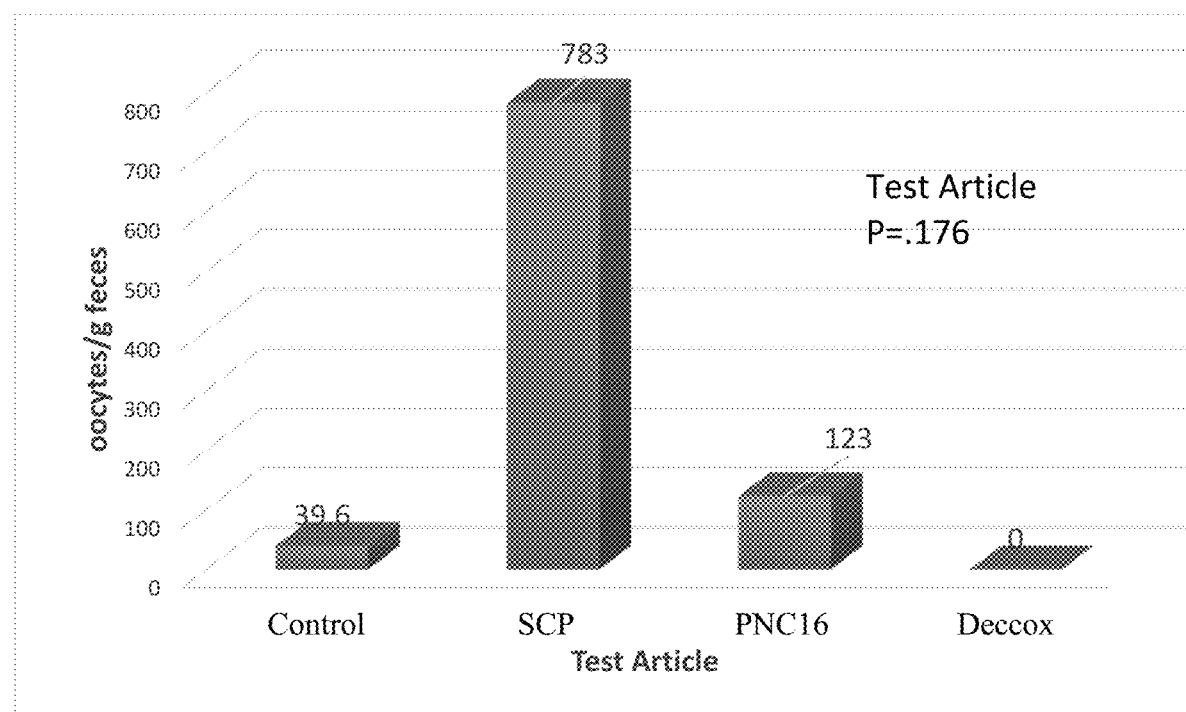
FIG. 3 is a bar graph showing Eimeria species (oocytes/g) in feces of calves at 21 days of age following treatment with different preparations as disclosed herein.
Figure 4:
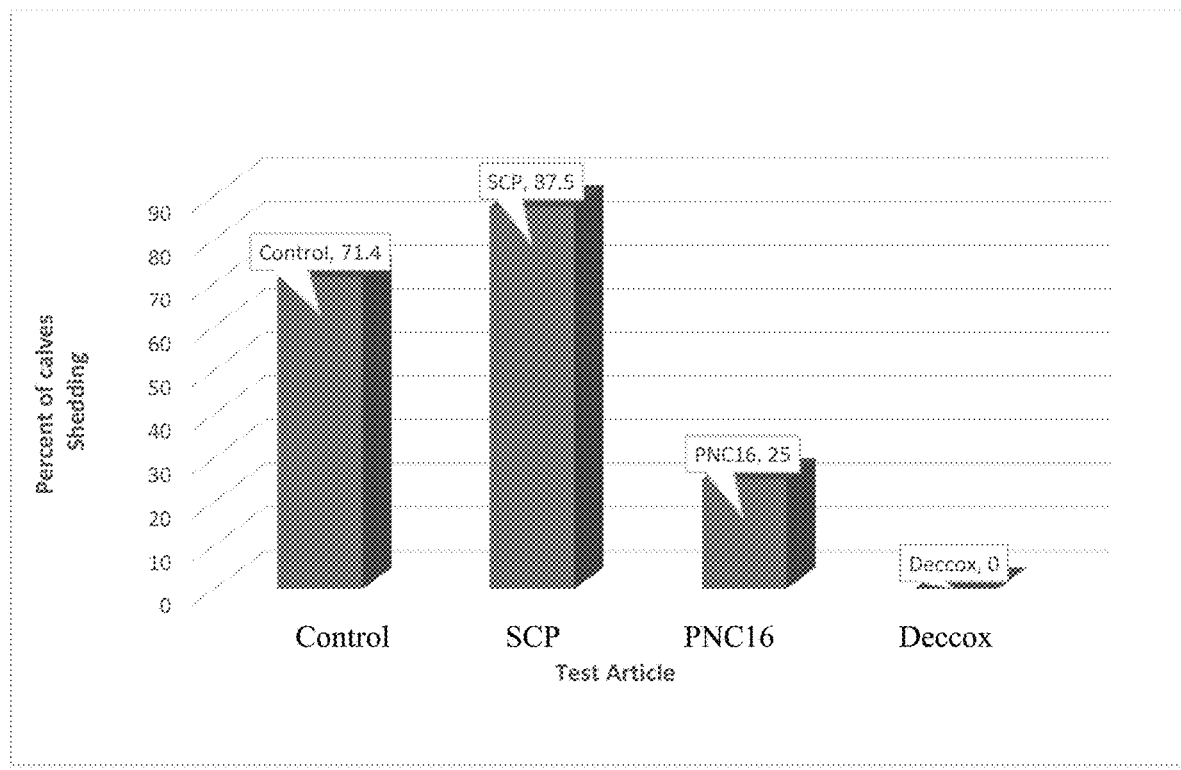
FIG. 4 is a bar graph showing the percentage of calves following treatment with different preparations as disclosed herein shedding Eimeria species in feces at 21 days of age.

Through day 14, *Cryptosporidium* oocytes were the only parasites detected. On day 21, in addition to *Cryptosporidium* oocytes, many species of Eimeria were also detected (FIG. 3) in particularly the SCP calves, which tended (p=0.10) to be higher than other test articles. Percent of Control and CEL calves shedding Eimeria were 71.5% and 85% respectively, whereas 25% and 0% of the PNC16 and DECCOX® calves were shedding Eimeria (FIG. 4).

*Cryptosporidium parvum*, commonly referred to as Crypto, is a protozoan (a one-celled organism) that causes diarrhea in calves (as well as other mammals). This extra cytoplasmic organism invades enterocytes (cells that line the intestines) in the distal small intestine and large intestine (Holland 1990). The infective stage of the life cycle of Crypto is the oocyst which is passed in the feces and which contains four sporozoites. When the oocyst is ingested the sporozoites are released. These sporozoites invade the cells in the intestine. Infection of cells leads to cell destruction and results in atrophy and fusion of intestinal villi. Oocyst shedding typically begins with diarrhea and continues for a few days passed clinical signs There is no effective treatment for Cryptosporidiosis. Morbidity is high with this disease but mortality is generally low. Moore (2003) showed no clinical benefit to administering decoquinate as a preventative treatment for cryptosporidiosis.

Coccidiosis is an infection of the small and large intestine caused by the protozoan parasites Eimeria zuernii and Eimeria bovid (Richards et al 2009). Without any preventive program the parasites invade the mucosal lining of the small and large intestines. Calves become infected by consuming the oocysts from fecal-contaminated feed, water, and bedding or by licking the hair of other contaminated calves. Clinical signs include diarrhea (watery to sometimes bloody), dehydration, weakness and depression. Drugs can be very useful in helping to prevent coccidiosis which include: Lasalocid or Boater 1 mg/kg per day, maximum 360 mg/day, Decoquinate or DECCOX® 22.7 mg/100 lb. daily for 28 days, or Monensin or Rumen sin 100 to 360 mg/head per day.

Thus, DECCOX® was not effective against Crypto, however, calves fed DECCOX® had no Eimeria shedding. PNC16 was as effective a DECCOX® in managing both Crypto and Coccidiosis.

In summary, during the conduct of in vivo testing, all calves were generally healthy and no animals died. There were no performance differences in calves due to test article, however, there was a tendency for calves fed PNC16 to gain more body weight than Control calves. In general, the 10-17-day period of life was characterized by increase temperature, fecal consistency score and fecal shedding in calves for all test articles, and the intensity was influenced by test article. PNC16 controlled rectal temperatures better than DECCOX® and as well as SCP. On day 14, temperatures were highest for calves receiving DECCOX® compared to PNC16. Fecal consistency scores were similar among test articles PNC16 performed like DECCOX® and SCP over the trial period, though from day 10-17, FCS were higher for SCP and PNC16 than Control and DECCOX®.

On day 7, fecal shedding of Crypto oocytes was highest for Control, with 70% of calves shedding. however, on day 14, >85% of all calves were shedding. DECCOX® calves numerically shedded the most *Cryptosporidium* oocytes, but not significantly higher than SCP, Control and PNC16.

PNC16 controlled Eimeria species shedding as well as DID an antibiotic (DECCOX®), and 6-fold better than SCP. No calves demonstrated Eimeria shedding until day 21, at which time, Control and SCP calves experienced >70% of calves shedding, whereas PNC16 and DECCOX® only had 25% and 0% of calves shedding respectively. There was a tendency for Eimeria shedding to be higher for calves receiving CEL compared to other treatments.

In vivo testing for health effects of lees-based preparations in early lactating cows The study was conduct at Spruce Haven Farms, Union Springs, N.Y., a commercial dairy consisting of 1800 mature cows. Thirty-two multiparous dry cows were balanced across 4 postpartum treatments by previous lactation 305 equivalent milk production. There were thirty calf hutches available to conduct the trial that were aligned in one row. At calving cows were housed in pens of eight cows each. Each pen contained deep bed sand free stalls with waters and head locks to a common bunk where the treatment diet was offered. The test articles evaluated included 3 different prebiotics incorporated into the diet via 225 g of corn meal to provide level according to manufacturer's recommendation. The treatments were as follows: Control (no test article, 225 g corn meal only), prebiotic CEL (28 g of CELMA-NAX™/cow/d blended with 197 g of corn meal), Omnigender-AF (56 g of OMNIGENDER™-AF prebiotic blended with 169 g of corn meal) and Wine Lees (WL), prepared as described above (3 g of a wine lees preparation blended with 222 g of corn meal). All test article blends were incorporated into a TMR that was the same for all treatments, except for the different 225 g test article inclusions.

Milk: Cows were milked trice daily (0400, 1200 and 2000 h) in a double 17 parallel milking parlor with sampling devices. All daily milkings were totaled for each cow within pen on study. Total daily milks were calculated to represent mean daily milk per cow for comparative purposes. Milk samples for composition were collected and composited from each cow at each of three milking's (20-ml aliquots/milking) on a weekly basis. Samples were preserved, frozen and slow thawed after all trial cows in each group completed each week. A weekly pen composite sample was created based on an average weighted weekly milk production per cow. Composite samples were submitted to Dairy One, Ithaca N.Y. for analysis of protein, fat, lactose and MUN by Milk Oscan (Foss Electric, Hellerud, Denmark) and somatic cell were determined by the Foss-o-mastic 5000 (Foss Electric, Hellerud, Denmark). The equation used for fat corrected milk was 3.5% FCM=(0.4255×milk (lb.))+[16.425×((fat %/100)×milk (lb.))]. Energy-corrected milk was calculated by the following equation: ECM=(kg milk× 0.327)+(kg milk fat×12.95)+(kg protein×7.2) (Shirley, 2006).

DMI Estimates. Daily group intakes were recorded throughout the trial period for each treatment pen. Total feed offered divided by total cows in the pen on a given day was calculated. Body weight and condition scores (Wildman et al., 1982) were taken on all animals at treatment initiation (day of calving), week 6 and termination from study (week 12). Blood was collected approximately 1 hr. before feed offering via tail vein on week 1 and 3 of trial for determination of NEFA and BHBA. Blood was collected in heparinized vacutainers, centrifuged and frozen. Samples were sent to Michigan State University (DCPAH, Lansing Mich.) for analysis.

Health. The following health indices were recorded: Retained placenta: placental membranes retained greater than 24 h after calving. Metritis was diagnosed by a purulent vaginal discharge. Ketosis: high urine ketone content with litmus strips. Displaced abomasums were detected by percussion with a stethoscope on either left or right side of the cow. Detection of new clinical mastitis cases was accomplished by the following procedure: At each milking, three fore strip ejections of milk from each quarter were evaluated for evidence of abnormal secretions (flakes, clots, stringy, creamy, and watery). If an abnormal secretion is observed, persistency was determined by stripping 6 to 8 more ejections. If the abnormal secretion persisted after 6 to 8 more ejections, the gland quarter was classified as clinical mastitis. A new clinical case on the same quarter was not declared until the infected quarter was free of abnormal secretion for at least 14 days after the declaration of normal saleable milk for that quarter.

Statistical analysis was by One-way ANOV using SAS JMP. When a time component was involved: milk and milk composition, the model was: TA (test article)+Time+TA× Time.

Effect of test articles on production performance of early lactation Holstein cows (1-21 days postpartum) is shown in Table 14.

TABLE 14

Effect of test articles on production performance of early lactation Holstein cows (1-21 d postpartum)

| Variable | Test Articles | | | | SEM | P= |
| --- | --- | --- | --- | --- | --- | --- |
| | Control | CEL | OMN | Wine Lees | | |
| | Yields | | | | | |
| 305 Equivalent | 24,500 | 24,743 | 24,455 | 24,548 | | |
| SD | 2,462 | 2,390 | 2,294 | 2,208 | | |
| N (cows/trt) | 8 | 8 | 8 | 8 | | |
| Milk, kg | $39.5^{ab}$ | $41.7^{ab}$ | $36.7^{b}$ | $43.2^{a}$ | 1.9 | 0.09 |
| 3.5% FCM, kg | $47.1^{ab}$ | $51.2^{ab}$ | $44.0^{b}$ | $52.7^{a}$ | 2.6 | 0.08 |
| ECM, kg | $46.4^{ab}$ | $50.6^{ab}$ | $43.4^{b}$ | $52.2^{a}$ | 2.5 | 0.07 |

TABLE 14-continued

Effect of test articles on production performance of
early lactation Holstein cows (1-21 d postpartum)

| | Test Articles | | | | | |
|---|---|---|---|---|---|---|
| Variable | Control | CEL | OMN | Wine Lees | SEM | P= |
| Fat, kg | $1.84^{ab}$ | $2.04^{ab}$ | $1.73^b$ | $2.09^a$ | 0.11 | 0.10 |
| Protein, kg | $1.33^{ab}$ | $1.46^{ab}$ | $1.25^b$ | $1.53^a$ | 0.08 | 0.09 |
| | | | Composition, % | | | |
| Fat | 4.66 | 4.89 | 4.77 | 4.80 | 0.16 | 0.79 |
| Protein | 3.37 | 3.49 | 3.40 | 3.51 | 0.10 | 0.74 |
| Lactose | 4.82 | 4.79 | 4.81 | 4.78 | 0.03 | 0.68 |
| MUN, mg/dL | 6.67 | 7.87 | 8.29 | 8.26 | 0.62 | 0.22 |
| SCC X1000 | 436 | 295 | 254 | 300 | 153 | 0.85 |

Milk production (Table 14) tended to be higher (p=0.09) for WL (43.2 kg) compared to Omni (36.7 kg), with Control (39.5 kg) and CEL (41.7 kg) not being different from either. This same tendency was demonstrated for FCM (p=008), ECM (p=0.07), Fat yield (p=0.10) and Protein yield (p=0.09). In all cases, levels produced by lactating cows administered an antimicrobial preparation as disclosed herein had higher production than cows administered any other treatment or controls, indicating a stimulatory effect of antimicrobial preparations as disclosed herein, such as produced from lees, on health and milk production. There were no significant effects of treatment on milk composition parameters.

Table 15 shows the effect of test article on health.

TABLE 15

The effect of test article on health

| | Control | CELMANAX ™ prebiotic | OMNIGEN ™-AF prebiotic | Wine Lees |
|---|---|---|---|---|
| n | 8 | 8 | 8 | 8 |
| | | Cows affected (% incidence) | | |
| Retained Placenta | 1 (12.5) | 0 | 0 | 0 |
| Metritis | 0 | 0 | 0 | 1 (12.5) |
| Ketosis | 1 (12.5) | 0 | 2 (25) | 1 (12.5) |
| Displaced Abom | 0 | 0 | 1 (12.5) | 0 |
| Hypocalcemia | 0 | 0 | 0 | 0 |
| Mastitis | 0 | 0 | 0 | 0 |
| Lameness | 1 (12.5) | 0 | 2 (25) | 1 (12.5) |

For Omni, 1 cow had ketosis and DA, for WL, one cow had metritis and ketosis

Cows consuming OMNIGEN™-AF prebiotic had the most incidence of metabolic disease, whereas cows fed CEL had no metabolic or infectious disease incidence in the first 21 days postpartum. Even though cows consuming WL contracted some metabolic diseases, they sustained milk production better than other treatments. Thus, an antimicrobial preparation as disclosed herein promoted health and healthy milk production from cows.

As demonstrated from the in vivo studies, antimicrobial preparations as disclosed herein had beneficial health effects when administered to cattle. Results are consistent with an antimicrobial effect as demonstrated from pro-agglutination and bacteriostatic effects. Importantly, the good health of cattle to whom antimicrobial preparations as disclosed herein were administered highlights the effectiveness of such preparations in inhibiting pathogenic microbes (including the pathogenic microbes disclosed herein against which preparations were tested for their agglutination, bactericidal, and bacteriostatic effects), to prevent illness and promote health, but without untoward effects resulting from interfering with normal gut bacteria required for proper and healthy digestion and wellbeing.

Furthermore, the effectiveness of antimicrobial YCW preparations as disclosed herein against a spectrum of different pathogenic microbes demonstrates that the health-enhancing effects achieved following administration to cows would also be found following administration to other animals, given that various pathogenic microbes that are susceptible to the herein-disclosed YCW antimicrobial preparations may cause illness in different species of animal. For example, antimicrobial YCW preparations as disclosed herein may promote the health of a mammal, such as a cow, ox, horse, goat, pig, sheep, horse, mule, donkey, deer, llama, cat, or dog, or other mammal. The animal may be a primate, such as a human. The animal may be a bird, such as a chicken, turkey, pheasant, goose, duck, quail, or other poultry.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprise" (and any form of comprise, such as "comprises" and "comprising"), "have" (and any form of have, such as "has" and "having"), "include" (and any form of include, such as "includes" and "including"), and "contain" (and any form contain, such as "contains" and "containing") are open-ended linking verbs. As a result, a method or device that "comprises", "has", "includes" or "contains" one or more steps or elements possesses those one or more steps or elements, but is not limited to possessing only those one or more steps or elements. Likewise, a step of a method or an element of a device that "comprises", "has", "includes" or "contains" one or more features possesses those one or more features, but is not limited to possessing only those one or more features.

The corresponding structures, materials, acts, and equivalents of all means or step plus function elements in the claims below, if any, are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of one or more aspects of the invention and the practical application, and to enable others of ordinary skill in the art to understand one or more aspects of the invention for various embodiments with various modifications as are suited to the particular use contemplated.

What is claimed is:

1. A method of making an antimicrobial composition, comprising:
   forming a fermentation residual yeast precipitate, adding one or more than one enzyme to the fermentation residual yeast precipitate, and heating the fermentation residual yeast precipitate at between 90° F. and 200° F., wherein
   the residual yeast precipitate is selected from wine lees and beer lees, and
   the one or more than one enzyme comprises a protease, a carbohydrase, or a combination of a protease and a carbohydrase.

2. The method of claim 1, wherein the one or more than one enzyme exposes a yeast inner cell wall carbohydrate of the fermentation residual yeast precipitate.

3. The method of claim 1, wherein forming comprises vinification from a varietal of grapes, the residual yeast precipitate comprises wine lees and the varietal of grapes is selected from chardonnay, pinot noir, cabernet sauvignon, cabernet franc, grenache, malbec, merlot, riesling, sauvignon blanc, semillon, syrah, tempranillo, viognier, and any combination of two or more of the foregoing.

4. The method of claim 3 wherein the varietal of grapes comprises chardonnay.

5. The method of claim 3 wherein the varietal of grapes comprises pinot noir.

6. The method of claim 3 wherein the varietal of grapes comprises cabernet franc.

7. The method of claim 3 wherein the yeast comprises a strain of yeast and the strain of yeast is selected from one or more *Saccharomyces* yeast strain, one or more *Brettanomyces* yeast strain, one or more *Candida* yeast strain, one or more *Kloeckera* yeast strain, one or more *Schizosaccharomyces* yeast strain, one or more *Aureobasidium* yeast strain, and any combination of two or more of the foregoing.

8. The method of claim 3 wherein the yeast comprises one or more *Saccharomyces* yeast strain.

9. The method of claim 8 wherein the one or more *Saccharomyces* yeast strain is selected from one or more *Saccharomyces cerevisiae* yeast strain, one or more *Saccharomyces bayanus* yeast strain, one or more *Saccharomyces beticus* yeast strain, one or more *Saccharomyces fermentati* yeast strain, one or more *Saccharomyces paradoxus* yeast strain, one or more *Saccharomyces pastorianus* yeast strain, one or more *Saccharomyces uvarum* yeast strain, and any combination of two or more of the foregoing.

10. The method of claim 3, wherein heating the fermentation residual yeast precipitate comprises heating the fermentation residual yeast precipitate at between 110° F. and 130° F.

11. The method of claim 1, wherein forming comprises brewing beer from a substance, the substance comprises barley, and the residual yeast precipitate comprises beer lees.

12. The method of claim 11, wherein the substance further comprises one or more of malt, molasses, honey, wheat, rye, rice, and oat.

13. The method of claim 11, wherein the yeast comprises a strain of yeast and the strain of yeast is selected from one or more *Saccharomyces* yeast strain, one or more *Brettanomyces* yeast strain, one or more *Candida* yeast strain, one or more *Kloeckera* yeast strain, one or more *Schizosaccharomyces* yeast strain, one or more *Aureobasidium* yeast strain, and any combination of two or more of the foregoing.

14. The method of claim 11, wherein the yeast comprises one or more *Saccharomyces* yeast strain.

15. The method of claim 14, wherein the one or more *Saccharomyces* yeast strain is selected from the group consisting of one or more *Saccharomyces cerevisiae* yeast strain, one or more *Saccharomyces bayanus* yeast strain, one or more *Saccharomyces beticus* yeast strain, one or more *Saccharomyces fermentati* yeast strain, one or more *Saccharomyces paradoxus* yeast strain, one or more *Saccharomyces pastorianus* yeast strain, one or more *Saccharomyces uvarum* yeast strain, or any combination of two or more of the foregoing.

16. The method of claim 11, wherein heating the fermentation residual yeast precipitate comprises heating the fermentation residual yeast precipitate at between 110° F. and 130° F.

17. A method of making an antimicrobial composition, comprising:
   adding one or more than one enzyme to wine lees, wherein the one or more than one enzyme comprises a protease, a carbohydrase, or a combination of a protease and a carbohydrase, and
   heating the wine lees at between 90° F. and 200° F.

18. The method of claim 17, wherein the wine lees was formed from making wine from a varietal of grapes and the varietal of grapes was selected from chardonnay, pinot noir, cabernet sauvignon, cabernet franc, grenache, malbec, merlot, riesling, sauvignon blanc, semillon, syrah, tempranillo, viognier, and any combination of two or more of the foregoing.

19. A method of making an antimicrobial composition, comprising:
   adding one or more than one enzyme to beer lees formed from brewing beer from barley, wherein the one or more than one enzyme comprises a protease, a carbohydrase, or a combination of a protease and a carbohydrase, and
   heating the beer lees at between 90° F. and 200° F.

20. The method of claim 19, further comprising wherein brewing beer from barley further comprised brewing beer from one or more of malt, molasses, honey, wheat, rye, malt, and oat.

21. The method of claim 1, further comprising reducing the water content of the fermentation residual yeast precipitate to less than 1% w/w.

22. The method of claim 17, further comprising reducing the water content of the wine lees to less than 1% w/w.

23. The method of claim 19, further comprising reducing the water content of the beer lees to less than 1% w/w.

* * * * *